(12) United States Patent
Ferrell et al.

(10) Patent No.: US 11,230,606 B2
(45) Date of Patent: *Jan. 25, 2022

(54) ANTI-PRO-N-CADHERIN ANTIBODIES AND METHODS OF TREATING PATHOLOGICAL FIBROTIC CONDITIONS AND TUMOR CELLS

(71) Applicant: Duke University, Durham, NC (US)

(72) Inventors: Paul Ferrell, Durham, NC (US); Salvatore Pizzo, Durham, NC (US); Robin Bachelder, Durham, NC (US)

(73) Assignee: Duke University, Durham, NC (US)

( * ) Notice: Subject to any disclaimer, the term of this patent is extended or adjusted under 35 U.S.C. 154(b) by 36 days.

This patent is subject to a terminal disclaimer.

(21) Appl. No.: 16/812,734

(22) Filed: Mar. 9, 2020

(65) Prior Publication Data

US 2020/0369779 A1    Nov. 26, 2020

Related U.S. Application Data

(60) Provisional application No. 62/829,842, filed on Apr. 5, 2019.

(51) Int. Cl.
*C07K 16/28* (2006.01)
*A61K 39/395* (2006.01)
*A61P 1/16* (2006.01)

(52) U.S. Cl.
CPC ............ *C07K 16/2896* (2013.01); *A61P 1/16* (2018.01); *C07K 2317/24* (2013.01); *C07K 2317/31* (2013.01); *C07K 2317/565* (2013.01)

(58) Field of Classification Search
None
See application file for complete search history.

(56) References Cited

U.S. PATENT DOCUMENTS

| | | | |
|---|---|---|---|
| 11,022,608 B2* | 6/2021 | Ferrell | ............ G01N 33/56966 |
| 2020/0103397 A1* | 4/2020 | Ferrell | .................... A61P 11/00 |
| 2020/0319166 A1* | 10/2020 | Ferrell | .................... A61P 11/00 |
| 2020/0369779 A1* | 11/2020 | Ferrell | ............... C07K 16/2896 |

OTHER PUBLICATIONS

Wahl et al. "N-cadherin-Catenin Complexes Form Prior to Cleavage of the Proregion and Transport to the Plasma Membrane" The Journal of Biological Chemistry, vol. 278, No. 19, Issue of May 9, pp. 17269-17276, 2003.

* cited by examiner

*Primary Examiner* — Phillip Gambel
(74) *Attorney, Agent, or Firm* — Banner & Witcoff, Ltd.

(57) ABSTRACT

Humanized antibody to a pathologically mislocated form of N-cadherin detects and eliminates cells that express the protein extracellularly. These cells are found in fibrotic conditions within heart, lung, and liver, as well as kidney, skin, and other organs effected by fibrosis. The antibody does not affect cells with normal, subcellular location of the protein.

14 Claims, 23 Drawing Sheets
(7 of 23 Drawing Sheet(s) Filed in Color)
Specification includes a Sequence Listing.

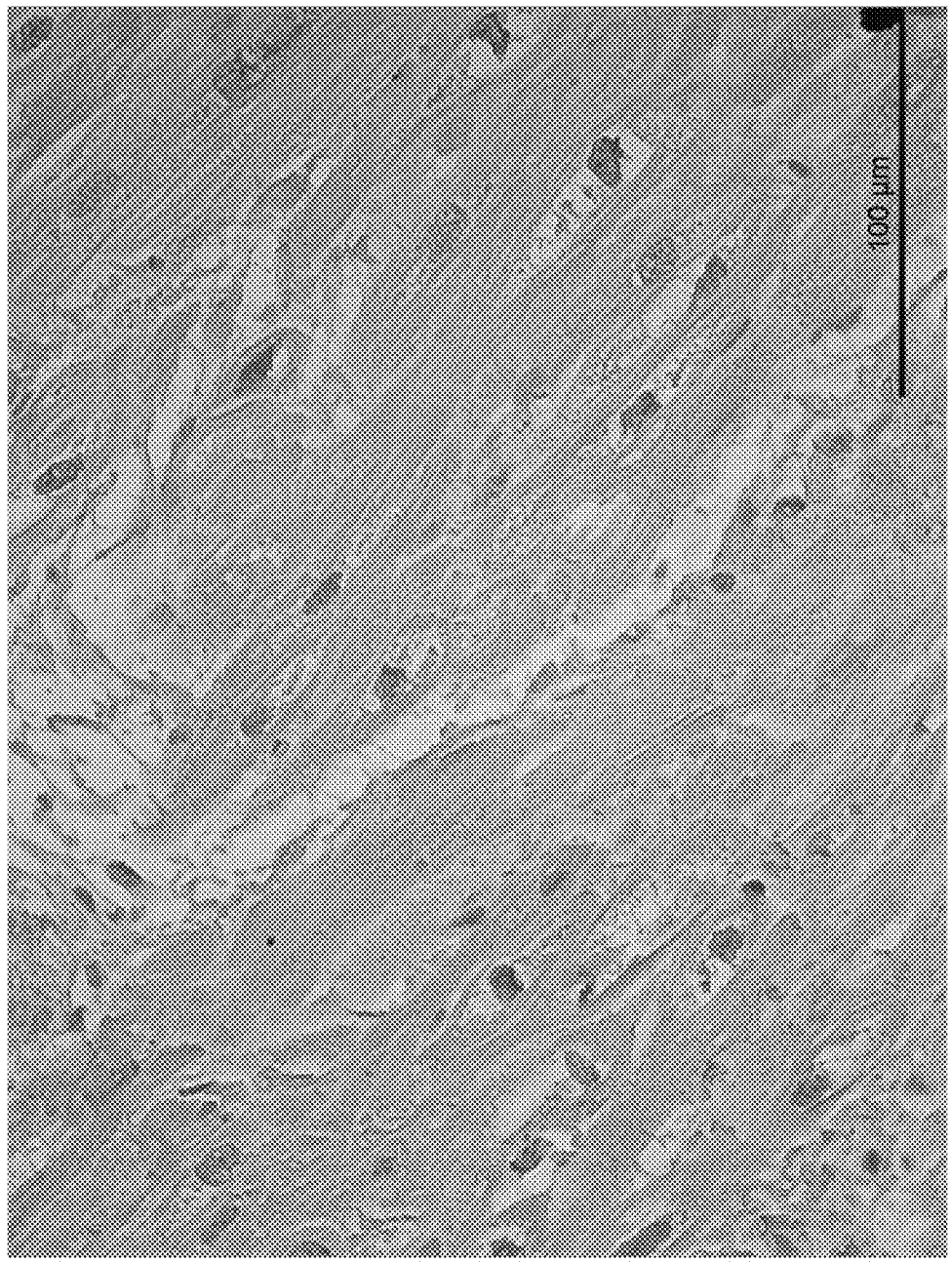
FIG. 2D Normal Human Atrial Tissue Trimmings From Implanted Heart

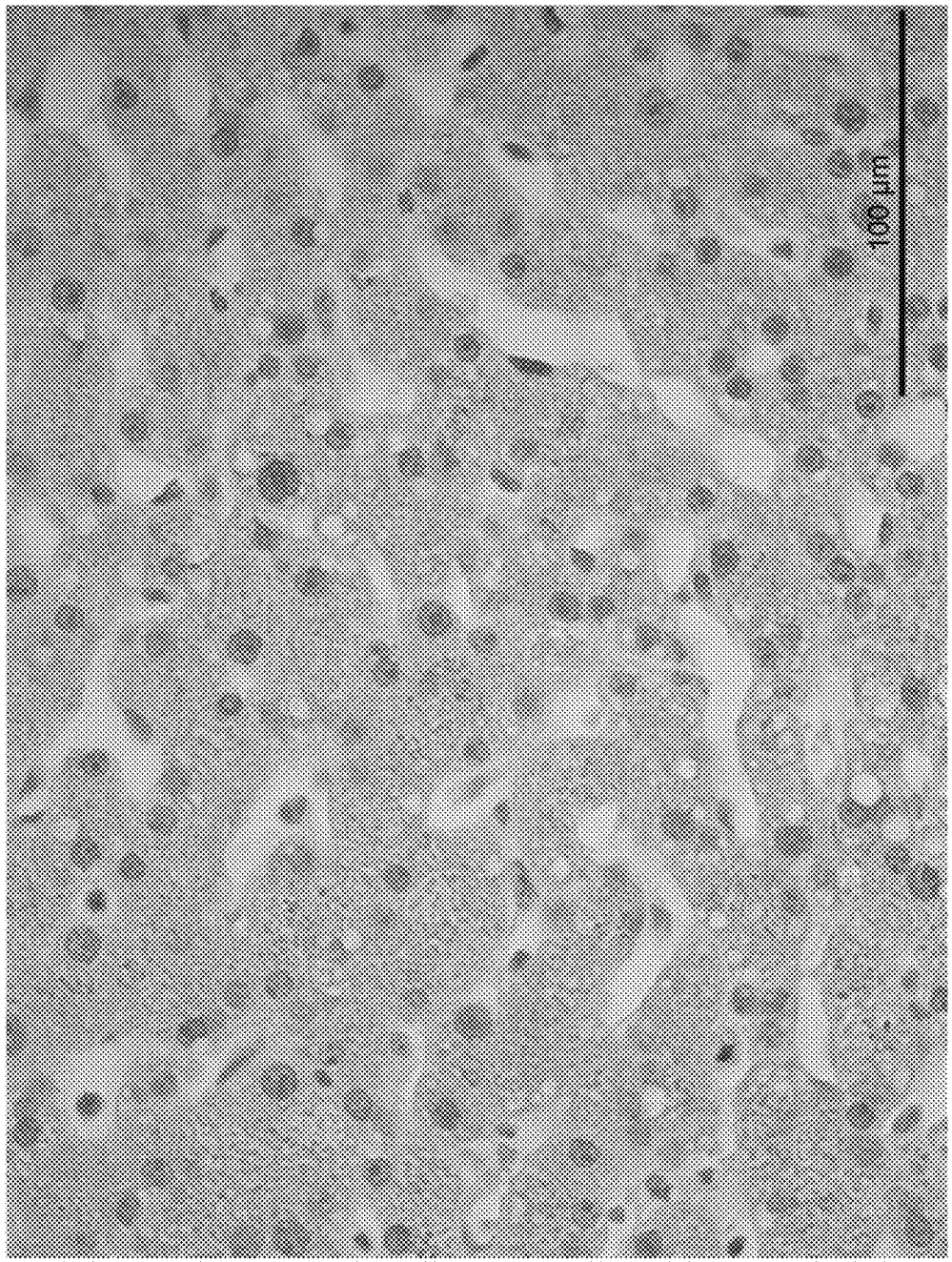
FIG. 2E Fatty Liver

Permeabilzation of Idiopathic Pulmonary Fibrosis Fibroblast LL97A

ANTI-PRO-N-CADHERIN ANTIBODIES AND METHODS OF TREATING PATHOLOGICAL FIBROTIC CONDITIONS AND TUMOR CELLS

TECHNICAL FIELD OF THE INVENTION

This invention is related to the area of immunotherapy. In particular, it relates to the use of antibodies for treating diseases associated with misprocessed or mislocated protein.

BACKGROUND OF THE INVENTION

Fibrosis is the aberrant remodeling of tissue architecture which results in loss of function and inevitably organ failure. It can arise in any organ in the body and manifest from many different disease origins; it is the major and only predictable gross physiological feature of many different diseases that is linearly correlated to organ failure. It is a biologically conserved process regardless of the organ of origin and common endpoint regardless of insult [1]. In the United States, 45% of all deaths can be attributed to some kind of chronic fibrotic related disease [2, 3]. Collectively, fibrotic disease kills more people than cancer. The current scientific theory describes fibrosis as the pathological and constitutive activation state of fibroblasts which result in excessive extracellular matrix turnover and deposition that interferes with normal organ function. Currently, an activated state of these fibroblasts is defined by their acquisition of alpha-smooth muscle actin (α-SMA) protein. Fibroblasts expressing this protein are defined as myofibroblasts, which are an extremely active, synthetic, tissue remodeling cell type. However, a true disease specific marker for these cells does not currently exist.

There is a continuing need in the art to detect and eliminate pathological cells involved in fibrosis.

SUMMARY OF THE INVENTION

According to one aspect of the invention a humanized antibody is provided. It specifically binds to pro-N-cadherin in its pro-domain. The humanized antibody comprises framework portions from a human antibody and six complementarity determining regions (CDRs) from a mouse antibody. The CDRs are SEQ ID NO: 22-27 or SEQ ID NO: 28-33.

Another aspect of the invention is a polynucleotide encoding a humanized antibody which binds to pro-N-cadherin in its pro-domain. The polynucleotide comprises segments encoding framework portions of a human antibody and segments encoding six complementarity determining regions (CDRs) from a mouse antibody. The segments encode CDRs having SEQ ID NO: 22-27 or 28-33. The segments may comprise SEQ ID NO: 5-10 or SEQ ID NO: 11-16.

Still another aspect of the invention is a method of treating a human with a pathological fibrotic condition. A humanized antibody is administered to the human. The number of pathological fibrotic cells is consequently reduced. The humanized antibody comprises framework portions from a human antibody and six complementarity determining regions (CDRs) from a mouse antibody. The six CDRs are SEQ ID NO: 22-27 or SEQ ID NO: 28-33.

Yet another aspect of the invention is a method of treating a human with a tumor. A humanized antibody is administered to the human. The number of tumor cells in the human is consequently reduced. The humanized antibody comprises framework portions from a human antibody and six complementarity determining regions (CDRs) from a mouse antibody. The six CDRs are SEQ ID NO: 22-27 or SEQ ID NO: 28-33.

According to another aspect of the invention a chimeric antibody which specifically binds to pro-N-cadherin in its pro-domain is provided. The chimeric antibody comprises framework portions from a non-murine antibody and six complementarity determining regions (CDRs) from a mouse antibody. The CDRs are SEQ ID NO: 22-27 or SEQ ID NO: 28-33.

These and other embodiments which will be apparent to those of skill in the art upon reading the specification provide the art with agents and methods for treating fibrotic diseases and tumors.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 2A-2F show that Pro-N-cadherin monoclonal antibody reacts specifically with the pro-domain of pro-N-cadherin from pathological myofibroblasts but not non-pathological. FIG. 2A. Fibroblasts and myofibroblasts from various origins were stained and analyzed by flow cytometry using pro-N-cadherin mAb (5 ug/mL), excluding dead cells via gating and 7AAD exclusion on Flowjo analysis software. Cell surface pro-N-cadherin positivity was found on myofibroblasts from pathological origins LL97A, CF-DCM, and LX2. Representative data of cardiac myofibroblasts from dilated cardiomyopathy (CF-DCM) were generated from myofibroblasts isolated from two separate explant patient hearts from DUMC. Pro-N-cadherin was not detected on primary normal human lung fibroblasts (NHLF), primary normal human cardiac fibroblasts (NHCF), or immortalized CCD-16Lu myofibroblast cell line from healthy donor. FIG. 2B. Total protein lysates were analyzed by western blot for each cell line. These corroborate pro-N-cadherin cell surface data. FIG. 2C. Immunohistochemistry (MC) performed for pro-N-cadherin was positive in patient tissue from cirrhotic liver and dilated cardiomyopathy but not normal liver. FIG. 2D. MC of normal human atrial tissue trimmings from implanted heart (with 10A10 pro-N-cadherin antibody). FIG. 2E. MC of fatty liver tissue (with 10A10 pro-N-cadherin antibody). FIG. 2F. IHC of heart-dilated cardiomyopathy, focus: Interstitial fibroblasts (with 10A10 pro-N-cadherin antibody).

FIG. 3A. Overnight treatment with pro-N-cadherin monoclonal antibody had no effect on NHLF viable cell numbers but significantly reduced the number of LL97A IPF myofibroblasts. FIG. 3B. Effects on proliferation from overnight treatment with pro-N-cadherin monoclonal antibody of CF-DCM and LX2 myofibroblasts was analyzed by relative BrdU amount incorporation into newly synthesized DNA. FIG. 3C. Short duration (1 hr) and time course (0.5-2 hr) treatment of cardiac myofibroblasts from DCM and IPF myofibroblasts, respectively, with pro-N-cadherin monoclonal antibody. LDH activity from the supernatants was used as a marker of cell membrane permeabilization and generalized cell death of myofibroblasts. FIG. 3D. CF-DCM cells were assessed for cell surface expression of pro-N-cadherin by flow cytometry after overnight pro-N-cadherin monoclonal antibody treatment [0.625 ug/mL] and compared to non-treated control. FIG. 3E. LX2 hepatic stellate myofibroblasts α-SMA gene expression measured by RT-PCR after overnight pro-N-cadherin monoclonal antibody [2 ug/mL] treatment relative to controls. Representative data from two different pro-N-cadherin monoclonal antibodies are shown. FIG. 3F. LL97 A α-SMA gene expression measured by rt-PCR after overnight pro-N-cadherin mAb [2 ug/mL] treatment relative to controls and normalized to GAPDH. FIG. 3G. LX2 cells were plated at $1 \times 10^3$ cells/well in 96-well plates and allowed to anchor overnight. Cells were treated with Pro-N-cadherin antibody 10A10 overnight and lifted with trypsin. For each condition, 3 wells were pooled together for each count. Cells were then stained with trypan blue and counted using the Bio-rad TC 20 automated cell counter. FIG. 3H. Primary cardiac fibroblasts from explant tissue were plated at $1 \times 10^3$ cells/well in a 96-well plate. Cells were treated with Pro-N-cadherin antibody 19D8 overnight and lifted with trypsin. Cells were then stained with trypan blue and counted using the Bio-rad TC 20 automated cell counter. FIG. 3I. Primary cardiac fibroblasts from explant tissue were plated at $1 \times 10^3$ cells/well in a 96-well plate. Cells were treated with Pro-N-cadherin antibody 19D8 overnight for 3 nights replacing the media and antibody each day. Cells were then trypsinized and stained with trypan blue and counted using the Bio-rad TC 20 automated cell counter. FIG. 3J. LL97 A cells were plated at $1 \times 10^3$ cells/well in 96-well plates and allowed to anchor overnight. Cells were treated with Pro-N-cadherin antibody 10A10 and BrdU overnight. BrdU incorporation was measured following the manufacturer's protocol (Millipore Sigma 11647229001).

Figure 1:
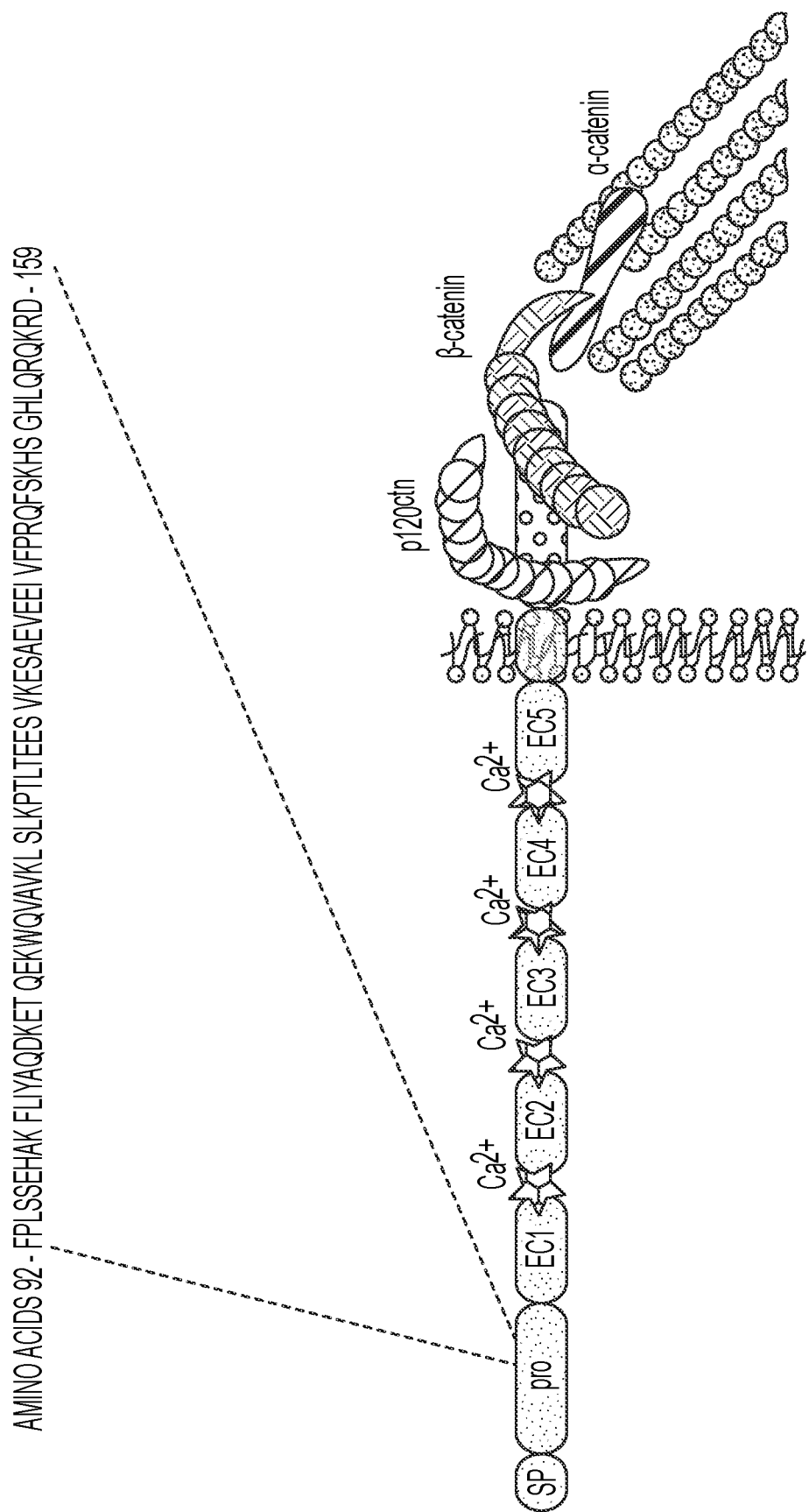
FIG. 1 is a schematic of the pro-N-cadherin molecule showing the sequence of nucleotides 92-159 of the pro-domain (SEQ ID NO: 1). The full domain runs from residue 22-159.

A sequence listing and table of sequences forms part of this application.

TABLES

The patent contains table(s) that have been included at the end of the specification.

DETAILED DESCRIPTION OF THE INVENTION

A humanized antibody or a chimeric antibody can be used in the human body with minimal adverse side effects arising from immune reactions to a foreign protein. The humanized or chimeric antibodies directed against pro-N-cadherin surprisingly detect and destroy pathological cells in the body which aberrantly localize pro-N-cadherin to the cell surface without the normal processing to form mature N-cadherin. In some cases, the cytotoxicity of the antibodies is accomplished using an attached cytotoxic moiety, such as a toxin, chemotherapy drug, or radionuclide.

Cell-surface located pro-N-cadherin serves as a specific target on a subpopulation of myofibroblasts that only exists in pathological settings. This specific target can distinguish a pathological fibroblast population from surrounding fibroblasts. This specific target of pathological fibroblasts has been found on the cell surface of patient derived myofibroblasts isolated from dilated cardiac myopathy, idiopathic pulmonary fibrosis, and the most well characterized hepatic stellate, myofibroblast cell line LX2, used for studying liver cirrhosis. Importantly, this specific target is not expressed on non-pathologic fibroblasts or myofibroblasts.

The specific target is a precursor to N-cadherin (i.e., pro-N-cadherin). Pro-N-cadherin is expressed on the surface of a subpopulation of myofibroblasts derived from several pathological settings of fibrosis, but not on myofibroblasts derived from physiologically normal tissues or on any other normal cell types [4]. It can serve as a disease-specific diagnostic biomarker and as a specific therapeutic target for fibrosis. Pro-N-cadherin is a precursor form of the protein N-cadherin. Pro-N-cadherin is normally processed in the Golgi apparatus of cells by furin proteases to produce the mature form, i.e., N-cadherin, from which the pro-domain has been removed. The processed, mature form is subsequently transported to the cell surface to serve as a cell adhesion molecule [4, 5]. Interestingly, some researchers have reported the presence of pro-N-cadherin on the surface of cancer [6, 7]. This aberrant phenomenon occurs in patient-derived tissues and myofibroblasts from fibrosis of the heart, lung, and liver. Thus, therapeutic targeting of cell-surface expressed pro-N-cadherin is useful for both fibrosis-associated diseases as well as cancers.

A murine monoclonal antibody binds to pro-N-cadherin on pathologic myofibroblasts, induces cell death in vitro, and rapidly eliminates this pathologic myofibroblast subpopulation without effecting fibroblasts or myofibroblasts isolated from normal tissue. The specificity of the murine monoclonal antibody is maintained in chimeric and humanized antibodies that share complementarity determining regions and/or variable domains.

The term "fibrosis" refers to those diseases/conditions associated with, or characterized by, fibrosis. Examples include, but are not limited to, respiratory conditions such as pulmonary fibrosis, cystic fibrosis, idiopathic pulmonary fibrosis, progressive massive fibrosis, scleroderma, obliterative bronchiolitis, Hermansky-Pudlak syndrome, asbestosis, silicosis, chronic pulmonary hypertension, AIDS associated pulmonary hypertension, sarcoidosis, tumor stroma in lung disease, and asthma; chronic liver disease, primary biliary cirrhosis (PBC), schistosomal liver disease, liver cirrhosis; cardiovascular conditions such as hypertrophic cardiomyopathy, dilated cardiomyopathy (DCM), fibrosis of the atrium, atrial fibrillation, fibrosis of the ventricle, ventricular fibrillation, myocardial fibrosis, Brugada syndrome, myocarditis, endomyocardial fibrosis, myocardial infarction, fibrotic vascular disease, hypertensive heart disease, arrhythmogenic right ventricular cardiomyopathy (ARVC), tubulointerstitial and glomerular fibrosis, atherosclerosis, varicose veins, cerebral infarcts; neurological conditions such as gliosis and Alzheimer's disease; muscular dystrophy such as Duchenne muscular dystrophy (DMD) or Becker's muscular dystrophy (BMD); gastrointestinal conditions such as Chron's disease, microscopic colitis and primary sclerosing cholangitis (PSC); skin conditions such as scleroderma, nephrogenic systemic fibrosis and cutis keloid; arthrofibrosis; Dupuytren's contracture; mediastinal fibrosis; retroperitoneal fibrosis; myelofibrosis; Peyronie's disease; adhesive capsulitis; kidney disease (e.g., renal fibrosis, nephritic syndrome, Alport's syndrome, HIV associated nephropathy, polycystic kidney disease, Fabry's disease, diabetic nephropathy, chronic glomerulonephritis, nephritis associated with systemic lupus); progressive systemic sclerosis (PSS); chronic graft versus host disease; diseases of the eye such as Grave's ophthalmopathy, epiretinal fibrosis, retinal fibrosis, subretinal fibrosis (e.g., associated with macular degeneration (e.g., wet age-related macular degeneration (AMD)), diabetic retinopathy, glaucoma, corneal fibrosis, post-surgical fibrosis (e.g., of the posterior capsule following cataract surgery, or of the bleb following trabeculectomy for glaucoma), conjunctival fibrosis, subconjunctival fibrosis; arthritis; fibrotic pre-neoplastic and fibrotic neoplastic disease; and fibrosis induced by chemical or environmental insult (e.g., cancer chemotherapy, pesticides, radiation/cancer radiotherapy). Any of these diseases may be treated with the antibodies to pro-N-cadherin described here.

The fibrosis-associated disease/disorder may be one of pulmonary fibrosis, atrial fibrillation, ventricular fibrillation, hypertrophic cardiomyopathy (HCM), dilated cardiomyopathy (DCM), non-alcoholic steatohepatitis (NASH), cirrhosis, chronic kidney disease, scleroderma, systemic sclerosis, keloid, cystic fibrosis, Crohn's disease, post-surgical fibrosis or retinal fibrosis. Any of these diseases may be treated with the antibodies to pro-N-cadherin described here.

Antigen binding fragments of humanized or chimeric antibodies, such as Fab and Fab2 fragments may also be used. The variable heavy (VH) and variable light (VL) domains of the antibody are involved in antigen recognition. Further confirmation was found by "humanization" of rodent antibodies, in which variable domains of rodent origin may be fused to constant domains of human origin such that the resultant antibody retains the antigenic specificity of the rodent parent antibody (see, e.g., Morrison et al (1984) Proc. Natl. Acad. Sd. USA 81, 6851-6855). In some embodiments, complementarity determining regions of the variable domains from a non-human source is substituted into a human antibody framework. Thus, less than the entire variable region is necessary to confer binding specificity.

Antibodies may be modified and selected by a process of affinity maturation in which a modified antibody is generated that has an improvement in the affinity of the antibody for antigen, compared to an unmodified parent antibody. Affinity-matured antibodies may be produced by procedures known in the art, e.g., Marks et al., Rio/Technology 10:779-783 (1992); Barbas et al. Proc Nat. Acad. Sci. USA 91:3809-3813 (1994); Schier et al. Gene 169:147-155 (1995); Yelton et al. J. Immunol. 155:1994-2004 (1995); Jackson et al., J. Immunol. 154(7):331 0-15 9 (1995); and Hawkins et al, J. Mol. Biol. 226:889-896 (1992). Affinity may be improved by greater than or equal to 1.5, 2, 3, 4, 5, 6, 7, 8, 9, 10, 15, 20-fold by this process.

Similarly, antibodies may be modified to remove features that may be problematic in the human body or problematic in a cell line used for production or manufacture. These modifications can be accomplished by site directed mutagenesis, for example. Examples of features that may be liabilities include T-cell epitopes, glycosylation sites, and deamidation. Codon optimization may be performed on a nucleic acid construct to use the most efficient codons for a particular amino acid sequence for expression in a particular species. This process may be done to adapt a sequence to a particular producer cell. For example, is a rodent cell is to be used, codons that are efficiently used and recognized in that rodent species may be substituted for the codons that were present in the donor or acceptor species of the antibody construct. This process typically enhances manufacturing rather than altering the product antibody itself.

To achieve a suitable therapeutic index, it is important that antibodies have and retain specificity for the pro-domain sequence and do not bind to other portions of the N-cadherin molecule. Other portions of the N-cadherin molecule are typically found on the cell surface, even in the non-diseased state. Recognition of other portions could lead to cytotoxicity to non-diseased cells that express non-pathological, mature N-cadherin on their cell surfaces.

Cytoxic agents or moieties that may be coupled to an antibody, preferably to a constant region of an antibody, but also possible to a variable domain, include bacterial toxins such as *Pseudomonas* exotoxin, diphtheria toxin, ricin A chain toxin, and saporin toxin. Chemotherapy drugs such as 2-(Hydroxymethyl)anthraquinone, Doxorubicin, methotrexate, and cyclopropanecarbonyl (CPC) chloridemay be used. Radionuclides emitting α-particles, β-particles or Auger electrons may be used as cytotoxic moieties.

Any type of human antibody can be used as a framework for humanization, including but not limited to IgA, IgD. IgE, IgG, and IgM. Antibodies may be, for example, IgG1, IgG2, IgG3, or IgG4. Chimeric antibodies and humanized antibodies may be seen as overlapping categories. The former may be used to denote a construct with entire variable regions from a non-human source, for example. The latter may be used to denote antibodies in which only the complementarity determining regions of an antibody are non-human. Both are non-naturally occurring constructed entities which aim to capitalize on and combine the beneficial properties of different species' antibodies. Variant humanized heavy and light chains of 10A10 and 19D8 antibodies are shown in SEQ ID NO: 35-39, 41-45, 47-51, 52-57. These retain the CDR sequences of the parent murine antibodies. A heavy chain variant from 10A10 may be used in combination with a light chain variant from 10A10. The two chains may derive from the same or a different variant. Similarly, a heavy chain variant from 19D8 can be used in combination with a light chain variant from 19D8. The two chains may derive from the same or a different variant.

Vectors for expression of antibody sequences may be, for example, episomes, viral, phage, artificial chromosomes, without limitation. Antibody sequences may be expressed in recombinant production systems, ranging from Gram-negative and positive bacteria, yeasts and filamentous fungi, insect cell lines, mammalian cells to transgenic plants and animals.

The above disclosure generally describes the present invention. All references disclosed herein are expressly incorporated by reference. A more complete understanding can be obtained by reference to the following specific examples which are provided herein for purposes of illustration only, and are not intended to limit the scope of the invention.

Figure 2A:
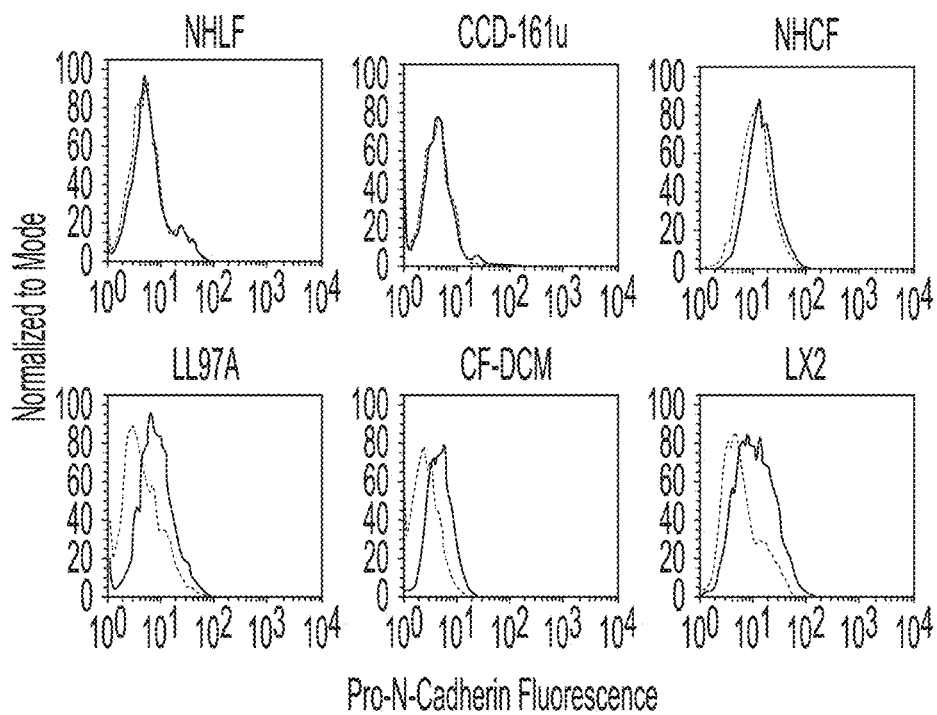
Figure 2B:
Figure 2C:
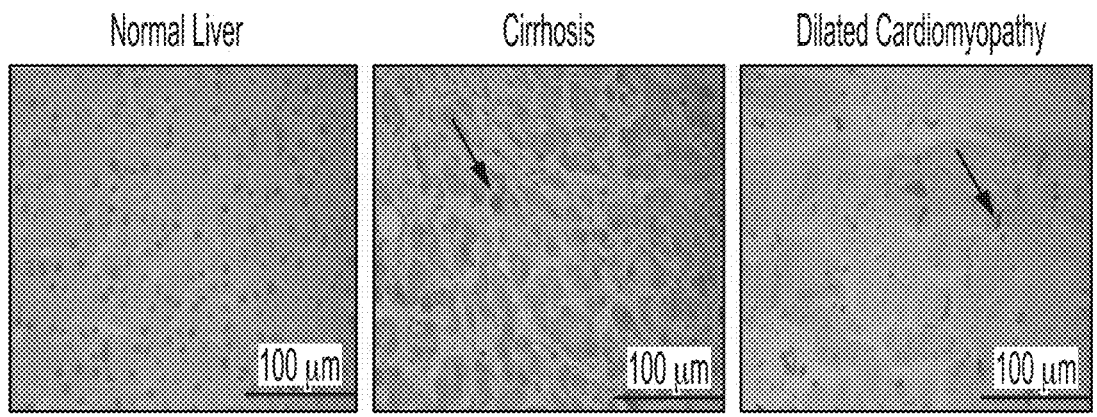
Figure 2F:
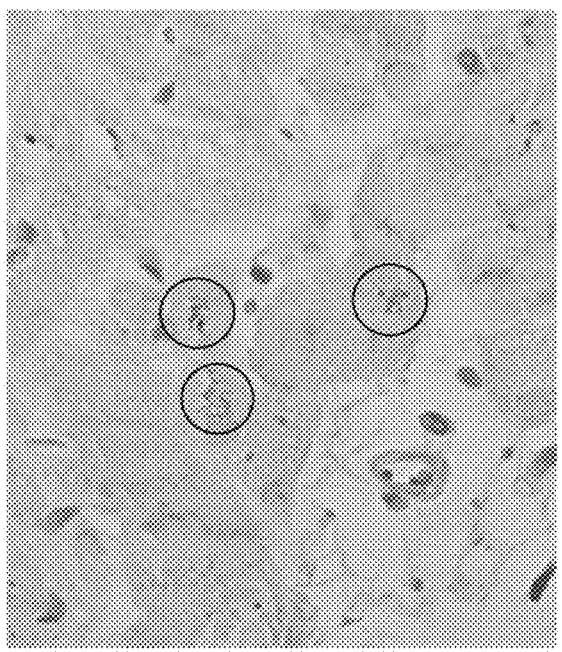

Example 1—a Monoclonal Antibody Specific for the Precursor (Pro) Domain of Pro-N-Cadherin Binds to Pathological Myofibroblasts from Lung, Heart and Liver but not Non-Pathological Fibroblasts and Myofibroblasts We investigated a murine monoclonal antibody (mAb) highly specific for the precursor (pro) domain of pro-N-cadherin[5]. Our studies show that this mAb recognizes pro-N-cadherin protein from human pathological myofibroblasts from lung (LL97A), heart (CF-DCM) and liver (LX2) (FIG. 2B). In addition, this antibody reacts with pro-N-cadherin on the cell surface of human pathological myofibroblasts from lung, heart and liver (FIG. 2A). Immunohistochemistry confirmed pro-N-cadherin protein expression in patient tissue derived from cirrhotic liver and dilated cardiomyopathy but not normal liver (FIG. 2C).

Figure 3A:
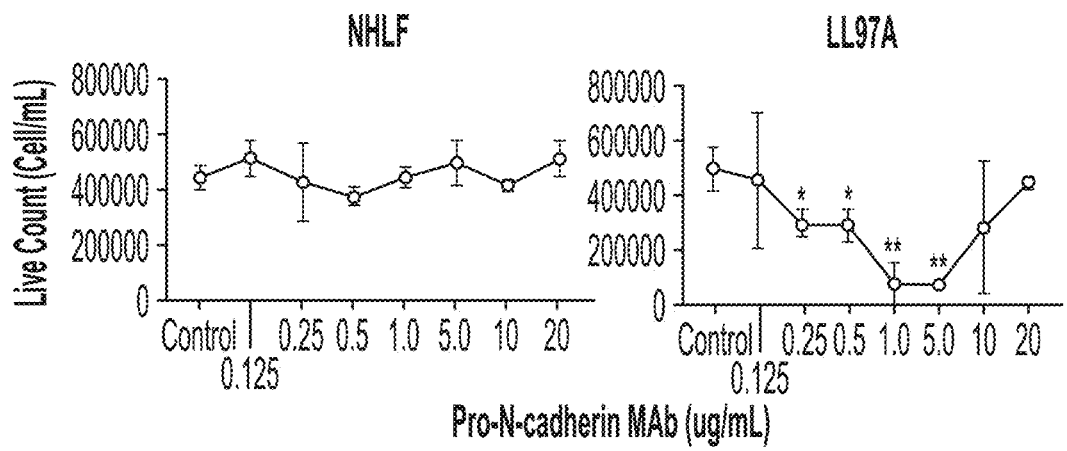
FIGS. 3A-3J show significantly reduced viable cell numbers and proliferation of pathological myofibroblasts as a result of pro-N-cadherin monoclonal antibody treatment at various concentrations.
Figure 3B:
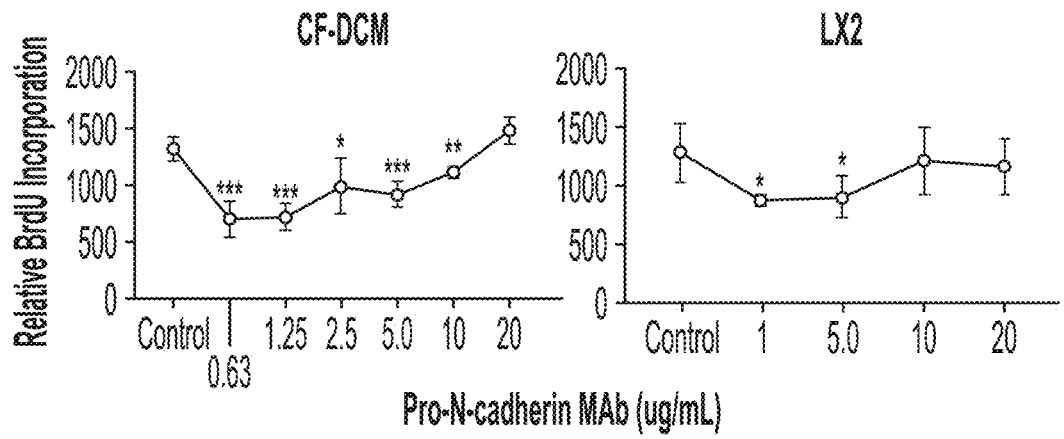
Figure 3C:
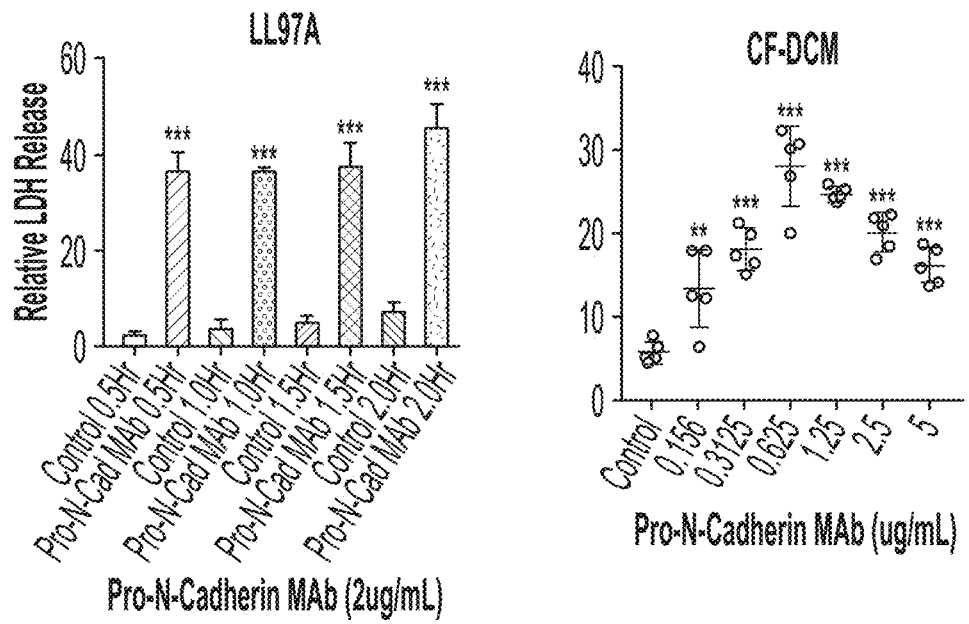
Figure 3D:
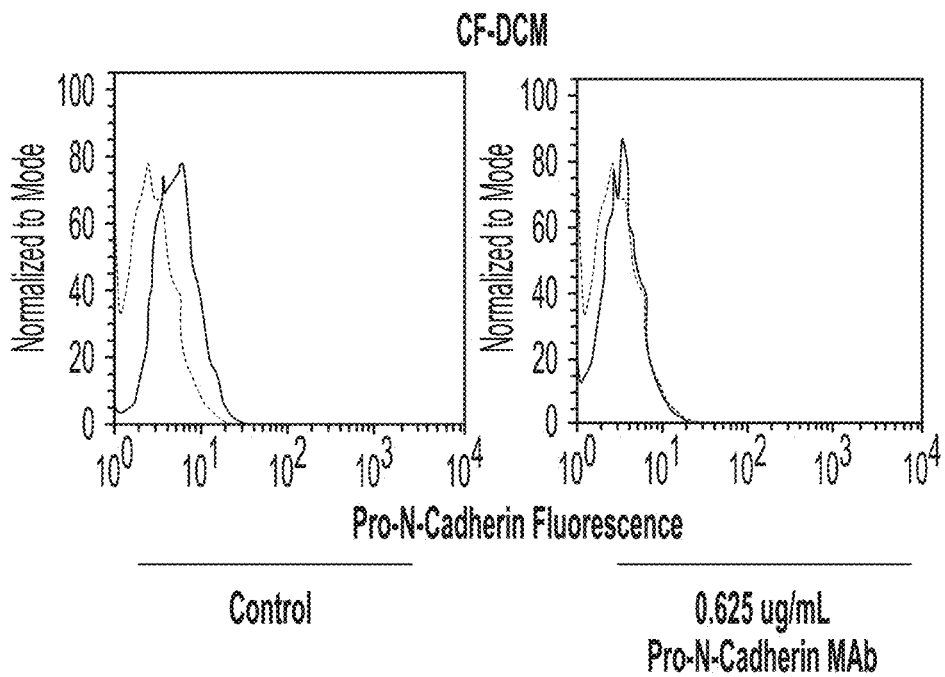
Figure 3E:
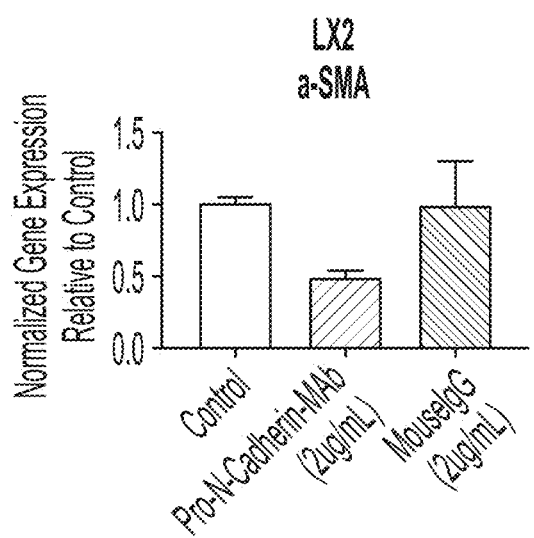
Figure 3F:
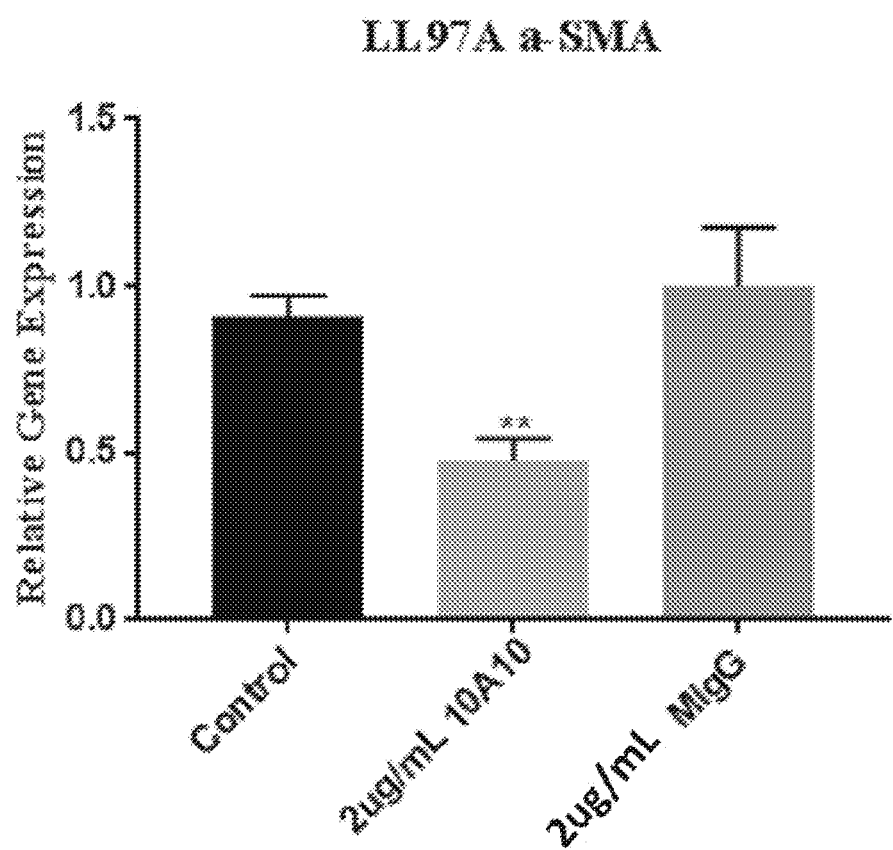
Figure 3G:
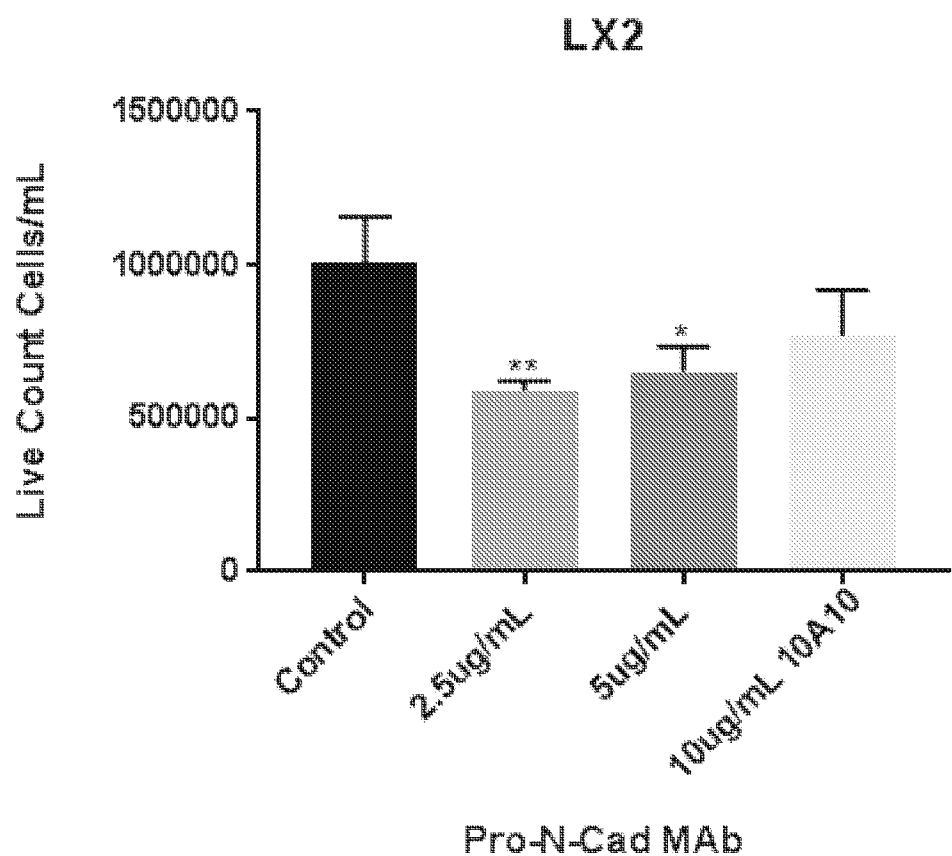
Figure 3H:
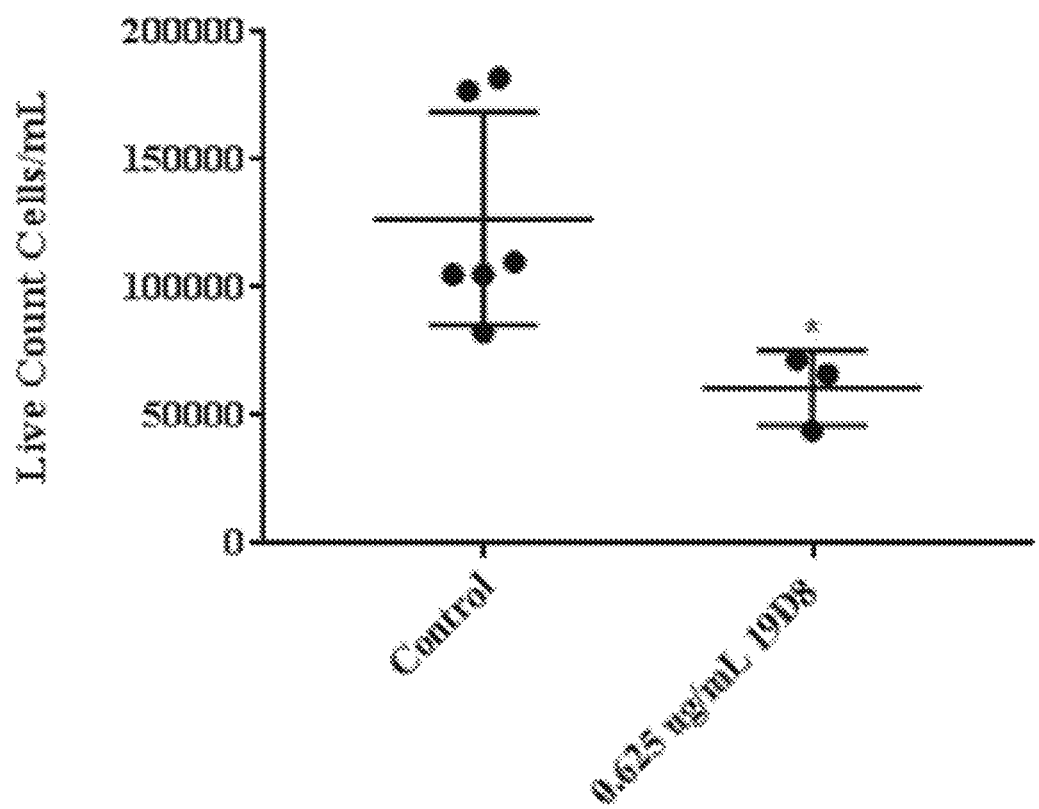
Figure 3I:
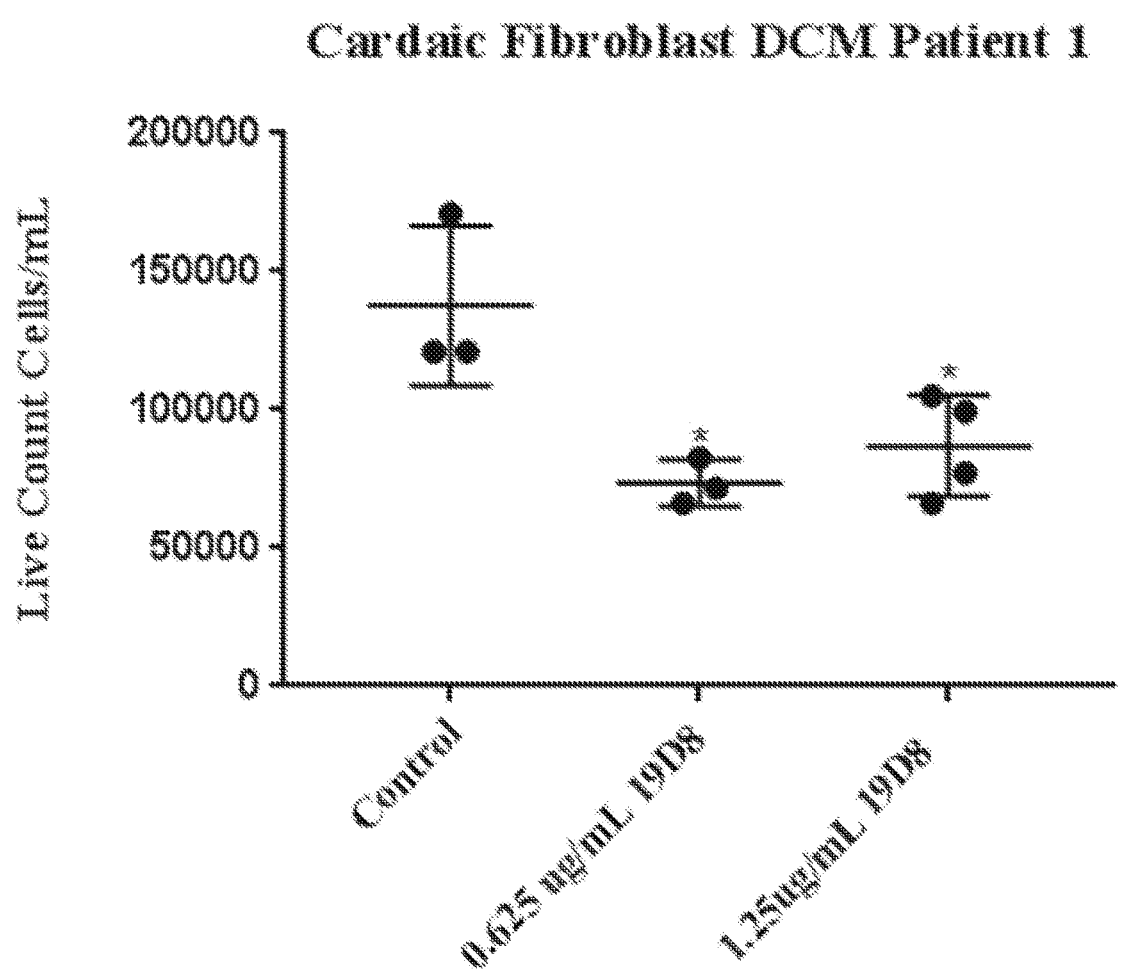
Figure 3J:
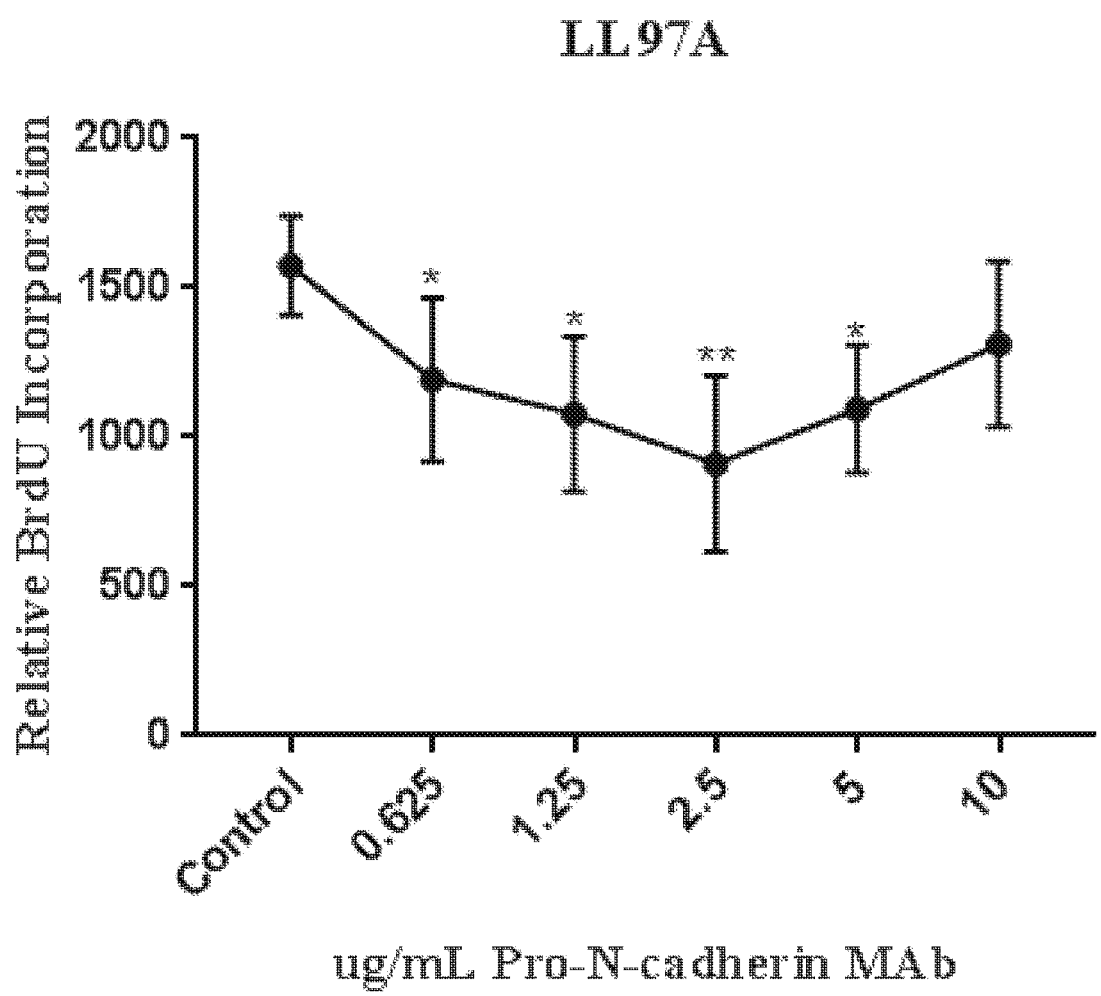
Figure 4:
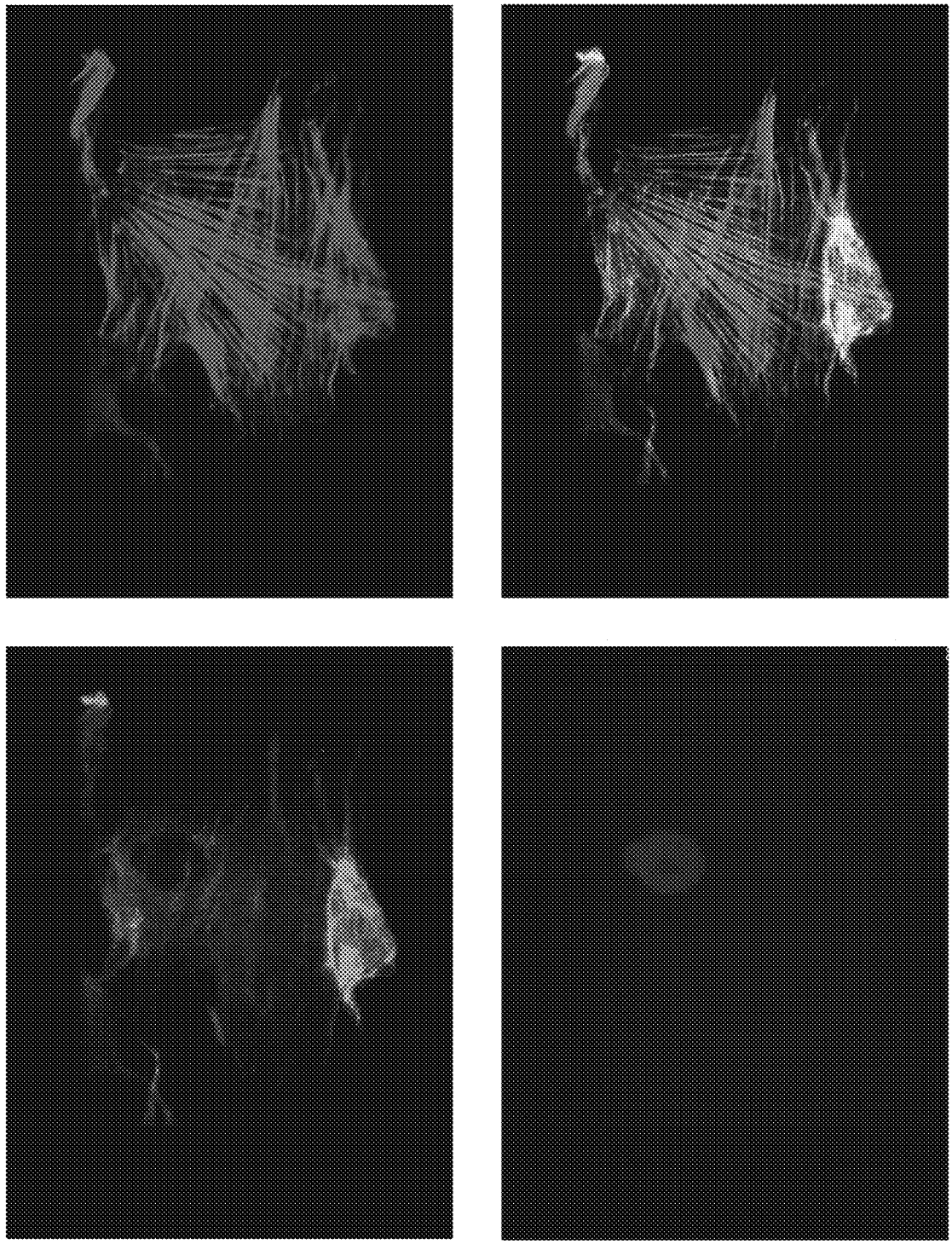
FIGS. 4, 5, and 6. LL97A Immunostaining. Image showing fibroblast cells expressing pro-N-cadherin (Green—Pro-N-cadherin; Red—Actin Cytoskeleton; Blue—Nuclei; Yellow—Actin/Pro-N-cadherin colocalization).
Figure 5:
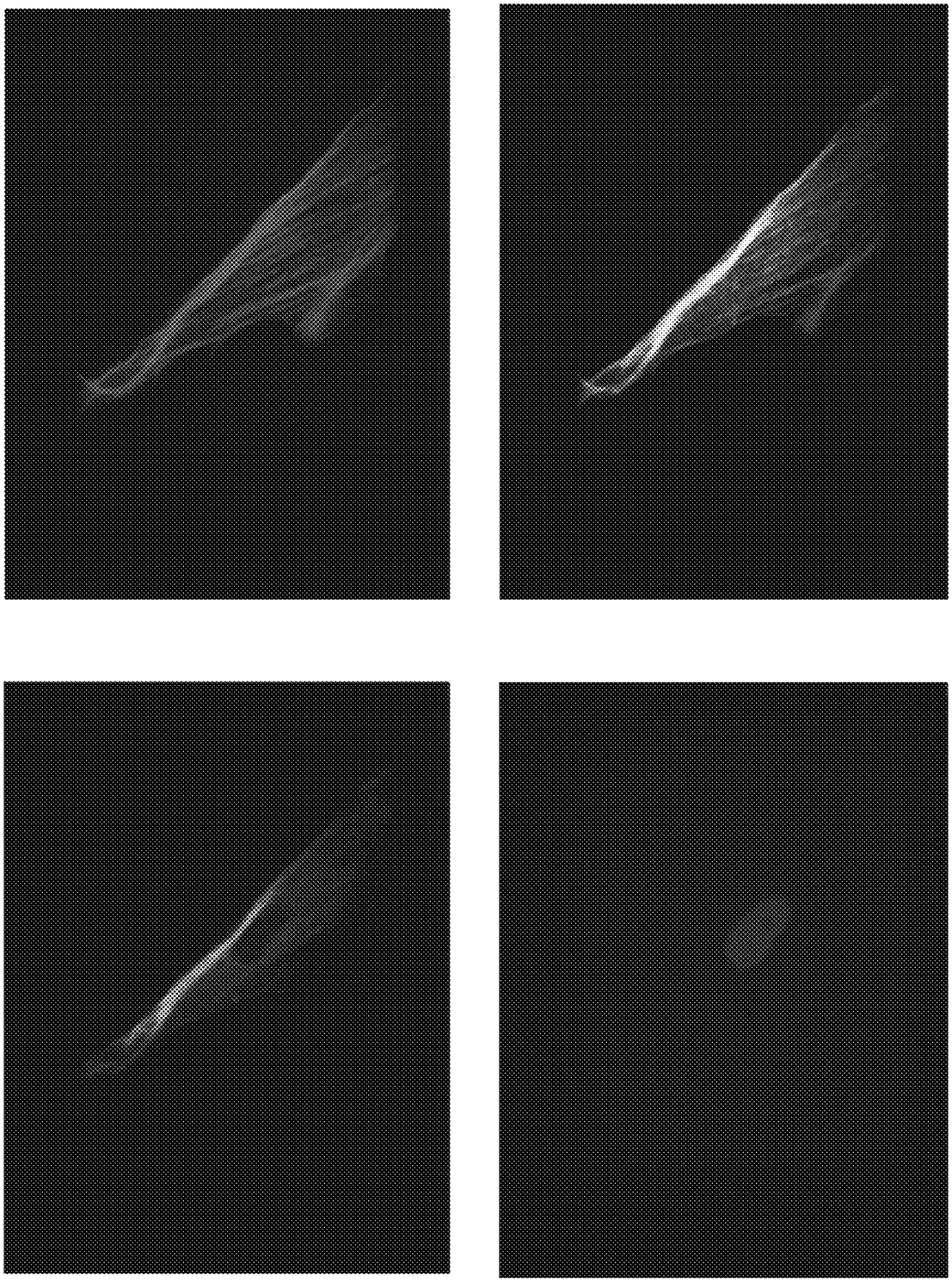
Figure 6:
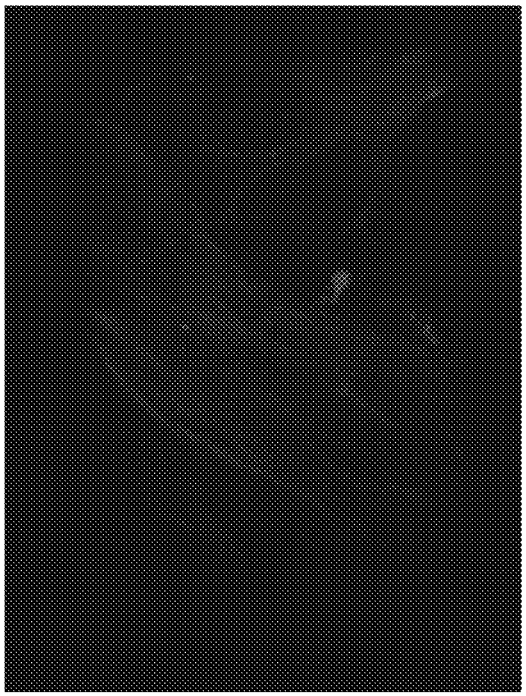
Figure 6:
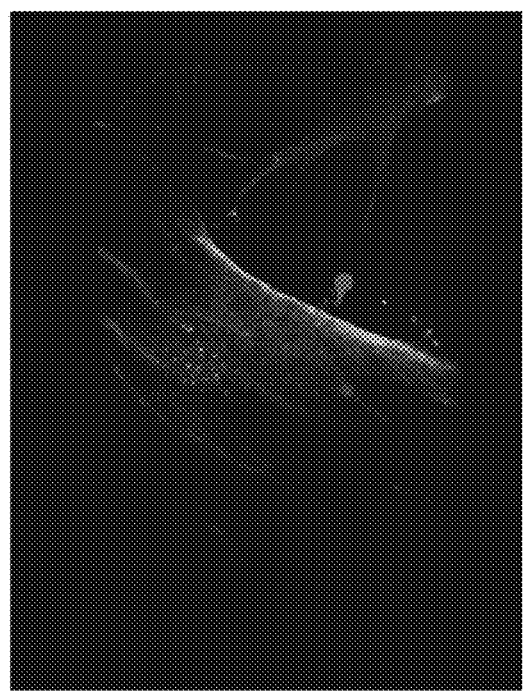
Figure 6:
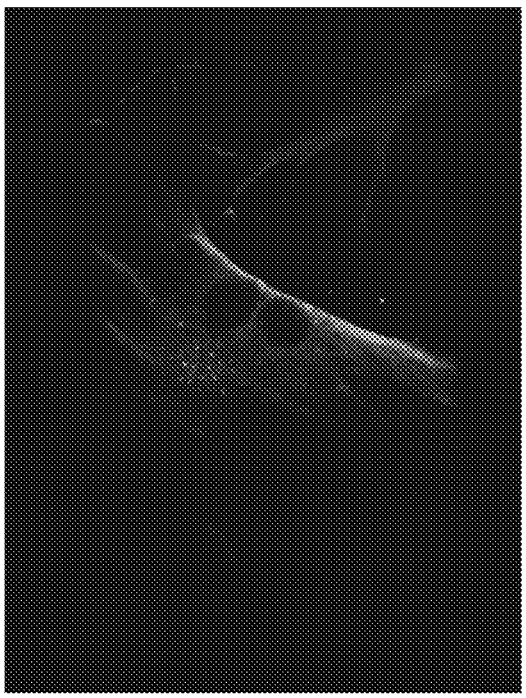
Figure 6:
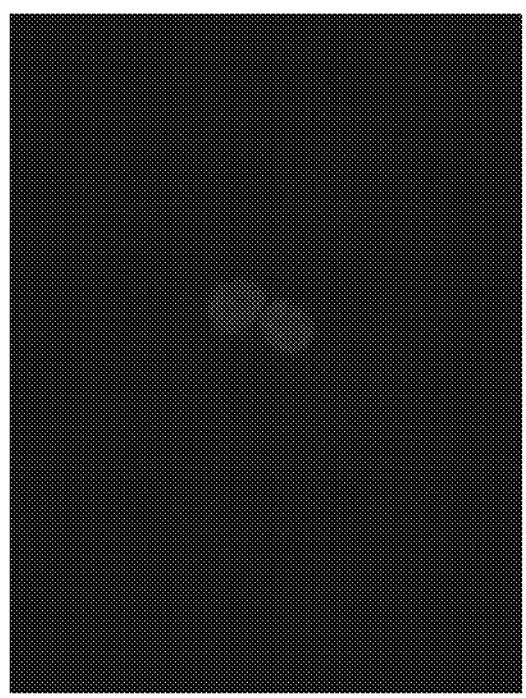
Figure 7:
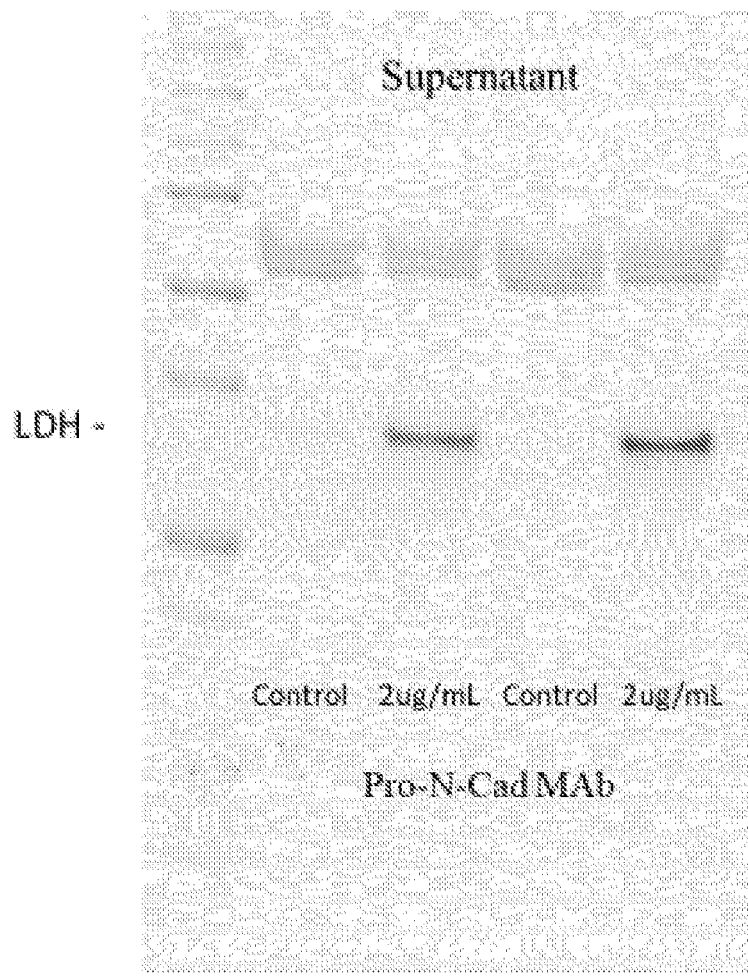
FIG. 7. Permeabilization of Idiopathic Pulmonary Fibrosis Fibroblast LL97A. LL97A cells were plated at $5 \times 10^4$ cells/well in a 6-well plate and allowed to anchor overnight. The following day, the media was replaced with serum free media. Cells were treated with Pro-N-cadherin antibody 10A10 for 4 hours, supernatant was removed and concentrated, and analyzed by western blot. Membrane was probed with LDH antibody.
Figure 8A:
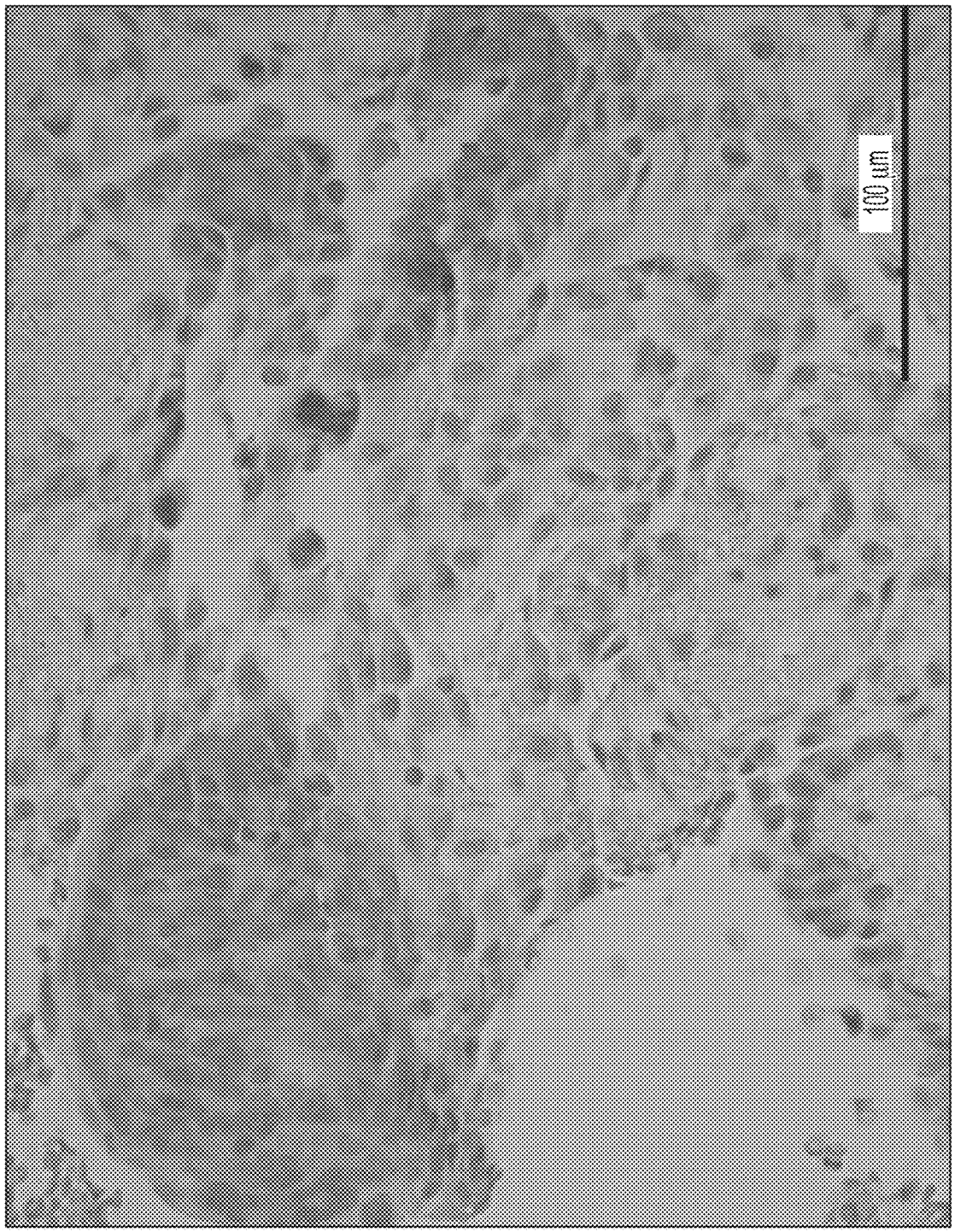
FIGS. 8A-8F shows immunohistochemistry of 3 patient tissues (some with multiple fields per tissue) stained with an antibody to pro-N-cadherin (PNC). These are representative of 10 patient samples tested and observed, all of which were positive for PNC. PNC is localizing to the alveolar epithelium; this localization indicates that this area of epithelium has undergone an epithelial to mesenchymal transition.
Figure 8B:
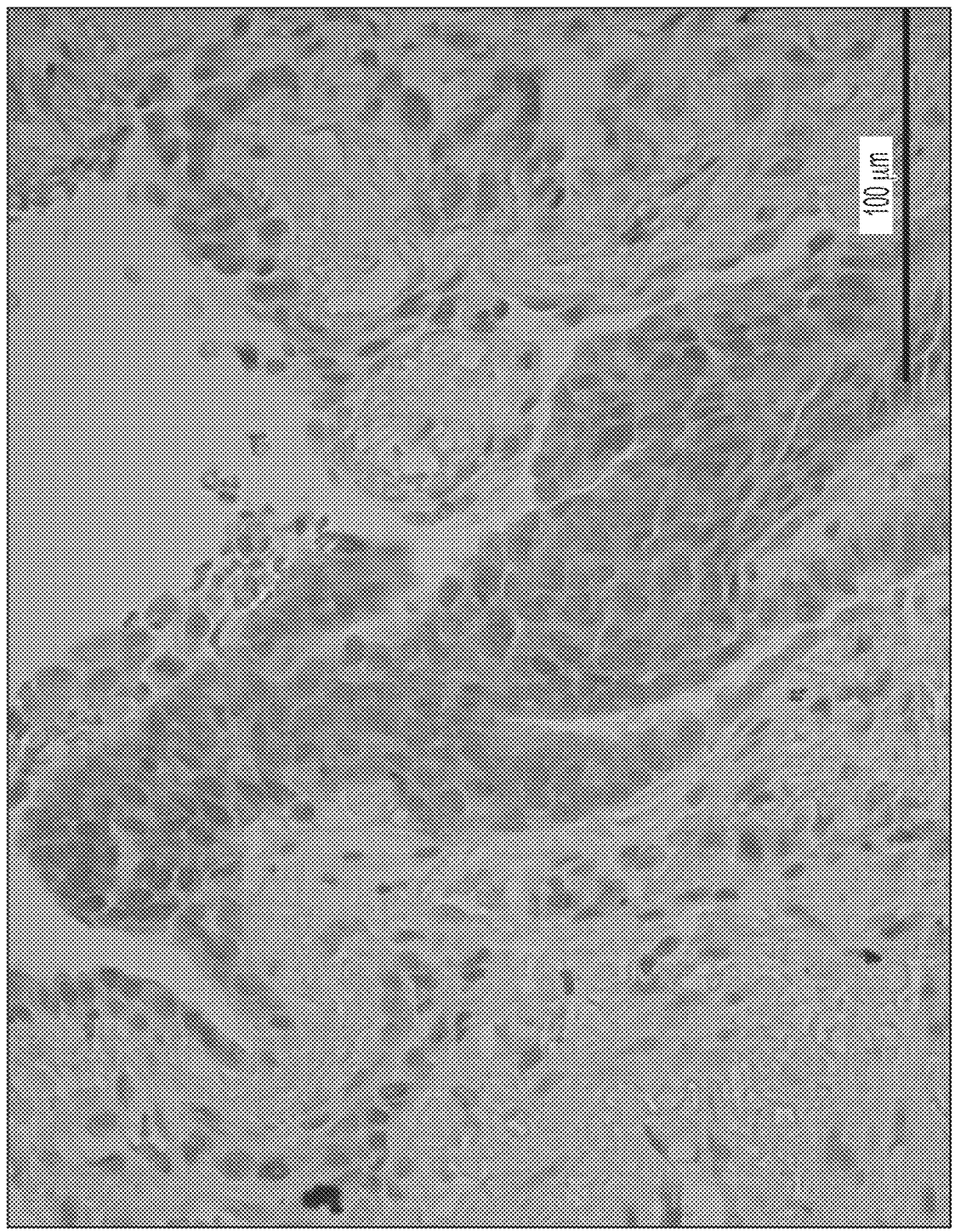
Figure 8C:
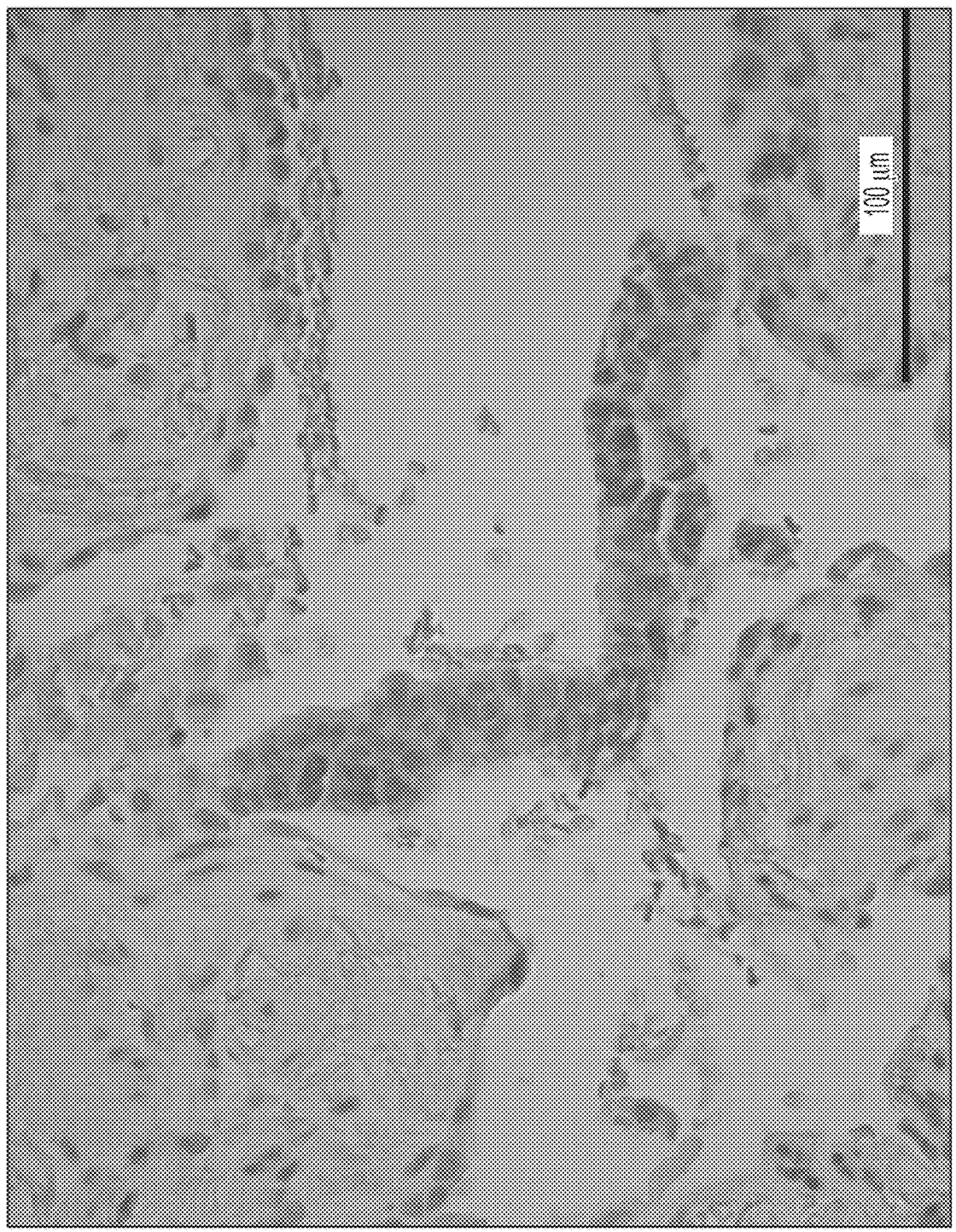
Figure 8D:
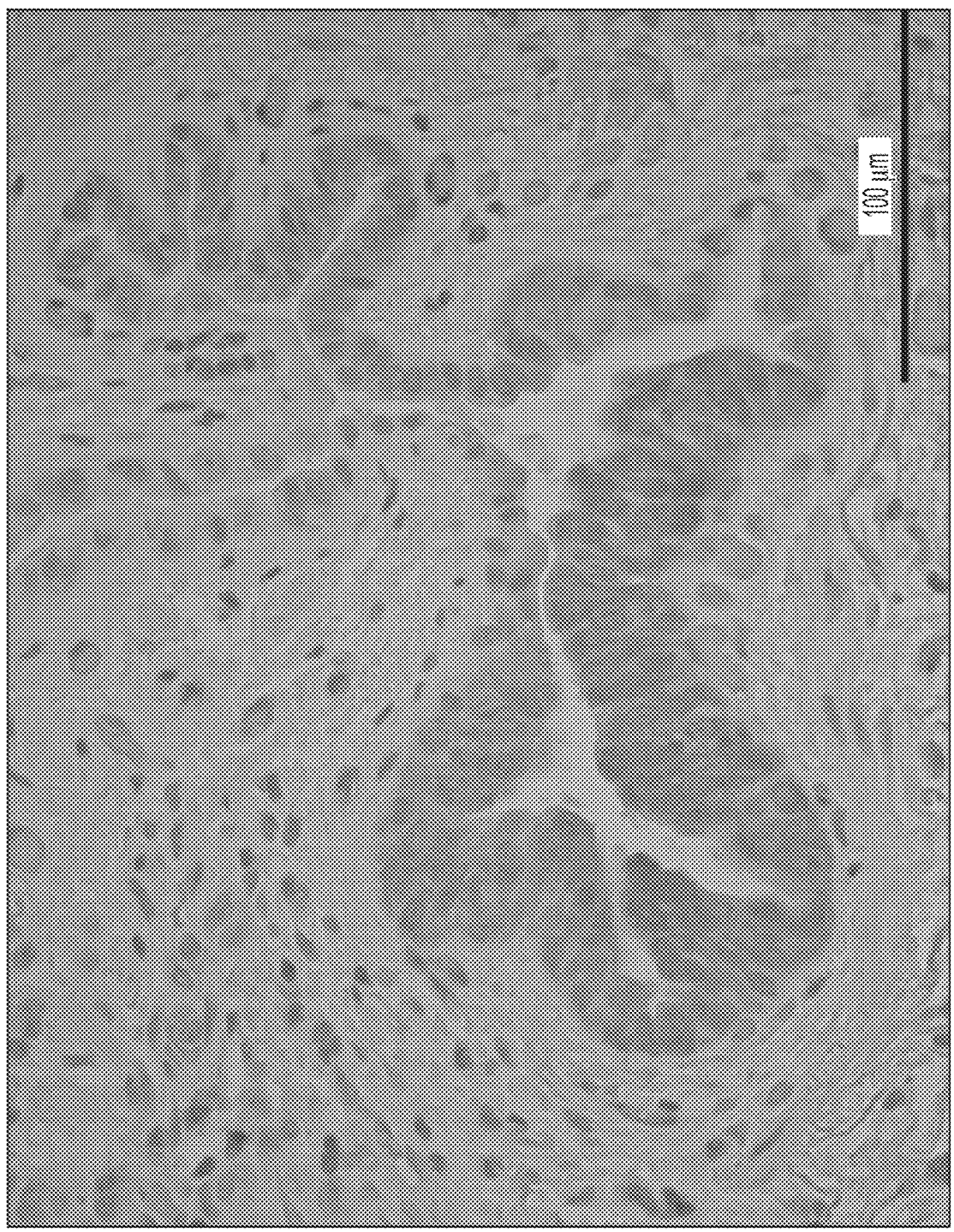
Figure 8E:
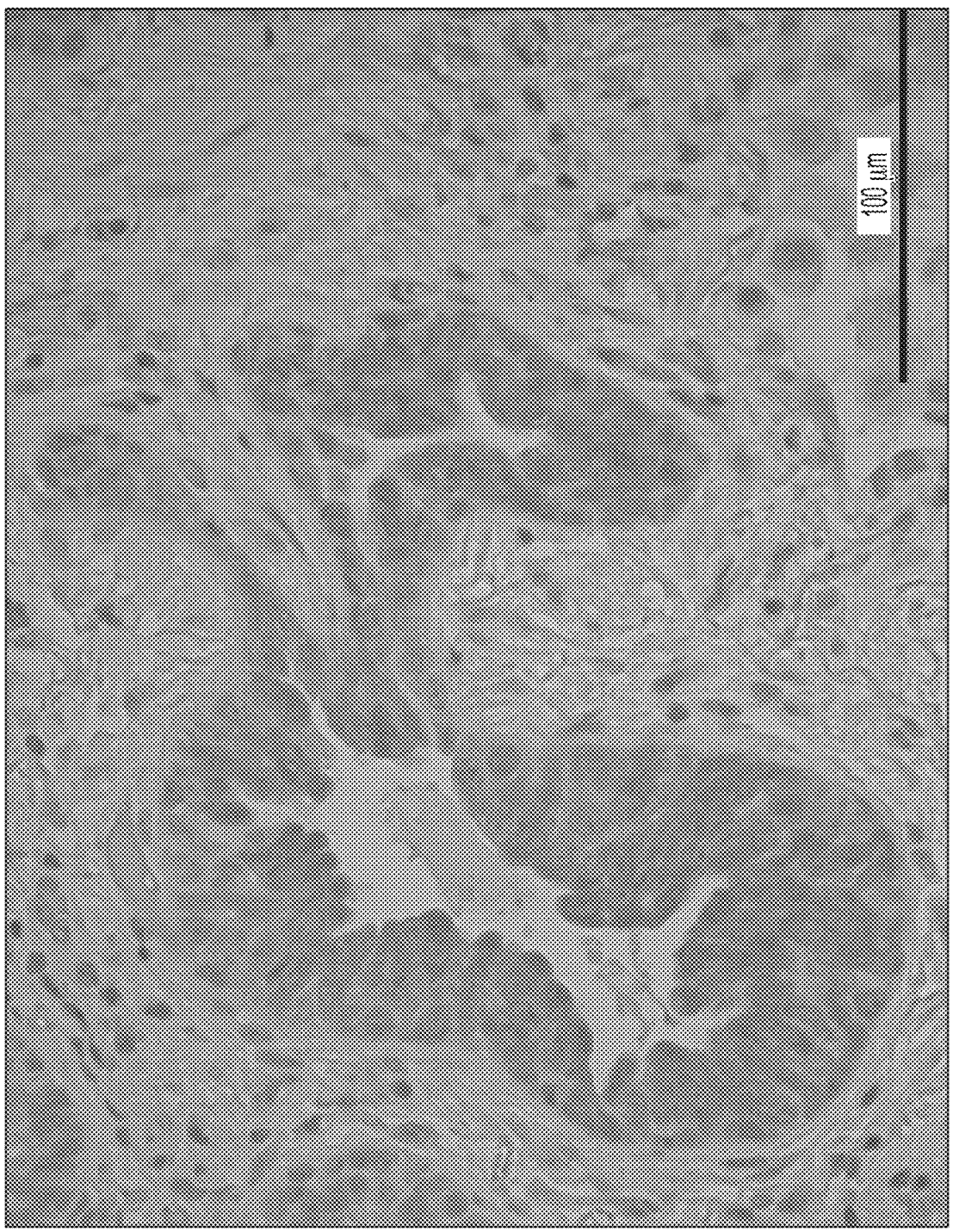
Figure 8F:
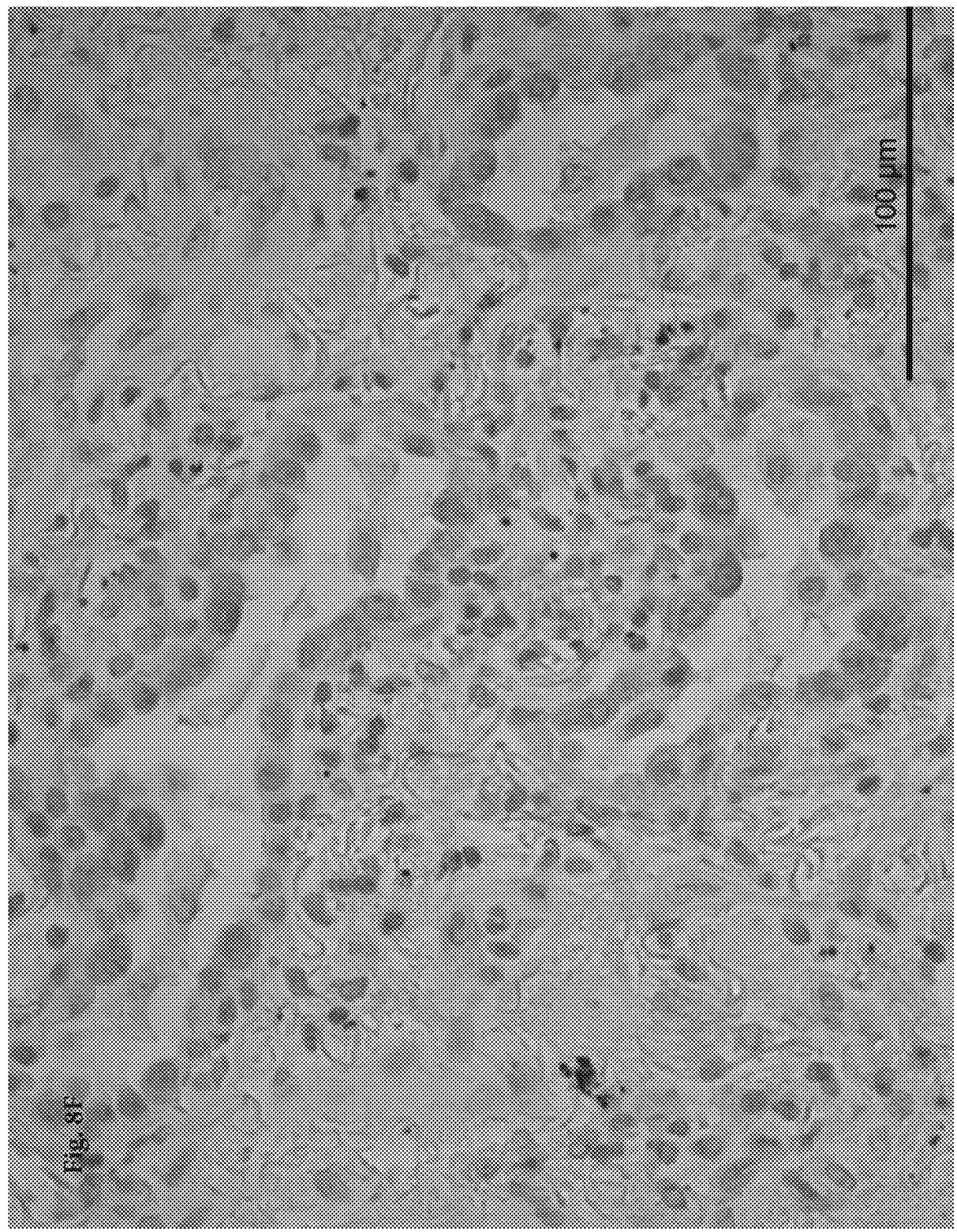
Figure 9:
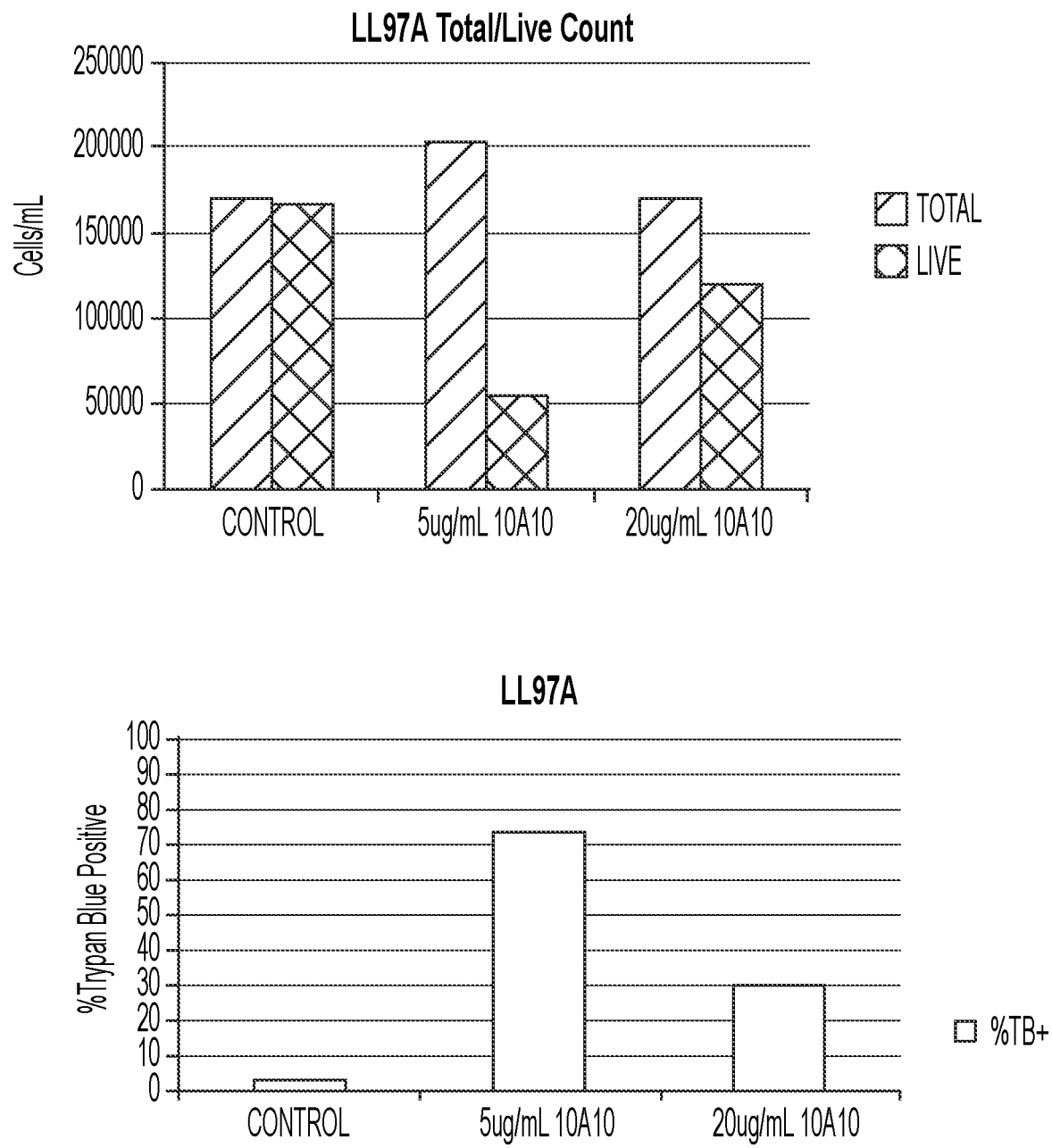
FIG. 9. Pro-N-Cadherin MAb is cytotoxic to fibroblast isolated from idiopathic pulmonary fibrosis. LL97A fibroblasts were plated at $1 \times 10^3$ cells/well in 96-well plates and allowed to anchor overnight. Cells were treated with Pro-N-cadherin antibody 10A10 overnight, lifted with trypsin, pooling 6-wells per condition. Cells were then stained with trypan blue and counted using the Bio-Rad TC 20 automated cell counter.

Example 2—the Effects of Pro-N-Cadherin mAb on Proliferation and Viability of Pathological Myofibroblasts Pathological myofibroblasts from heart, lung and liver were challenged with pro-N-cadherin mAb and effects were measured by several proliferation assays, flow cytometry, cytotoxicity assays, dose titrations and time course in vitro. Dose titrations of the monoclonal antibodies revealed the hook effect on each pathological myofibroblast culture tested by proliferation and cytotoxicity assays (FIGS. 3A, 3B and 3C). FIGS. 3A-3C demonstrate an example of the hook effect, in which the epitope is saturated by competitive binding of the mAb at high monoclonal antibody concentrations. The hook effect is a well characterized phenomenon, exclusively indicative of monoclonal antibody activity [8, 9]. In this case, when the epitope is saturated, steric hindrance limits antibody-antigen interactions to monovalent binding that limits crosslinking of the pro-N-cadherin antigen and decreases efficacy. At optimal concentrations, the antibody binds bivalently and optimal efficacy of cytotoxicity and reduced proliferation is observed. Furthermore, after overnight treatment of CF-DCM with optimal mAb concentration, the pathological subpopulation of myofibroblasts can no longer be detected by measuring cell surface pro-N-cadherin of the remaining myofibroblast culture via flow cytometry (FIG. 3D). Significantly reduced α-SMA gene expression was also observed after LX2 hepatic stellate myofibroblasts were treated with pro-N-cadherin mAb overnight (FIG. 3E).

REFERENCES

The disclosure of each reference cited is expressly incorporated herein.
1. Rockey, D. C., P. D. Bell, and J. A. Hill, *Fibrosis—a common pathway to organ injury and failure*. New England Journal of Medicine, 2015. 372(12): p. 1138-1149.
2. Wynn, T., *Cellular and molecular mechanisms of fibrosis*. The Journal of Pathology: A Journal of the Pathological Society of Great Britain and Ireland, 2008. 214(2): p. 199-210.
3. Wynn, T. A., *Fibrotic disease and the T H 1/T H 2 paradigm*. Nature Reviews Immunology, 2004. 4(8): p. 583.
4. Ozawa, M. and R. Kemler, *Correct proteolytic cleavage is required for the cell adhesive function of uvomorulin*. The Journal of Cell Biology, 1990. 111(4): p. 1645-1650.
5. Wahl, J. K., et al., *N-cadherin-catenin complexes form prior to cleavage of the proregion and transport to the plasma membrane*. Journal of Biological Chemistry, 2003. 278(19): p. 17269-17276.
6. Maret, D., et al., *Surface expression of precursor N-cadherin promotes tumor cell invasion*. Neoplasia, 2010. 12(12): p. 1066-1080.
7. Nelson, E. R., et al., *Chemotherapy enriches for an invasive triple-negative breast tumor cell subpopulation expressing a precursor form of N-cadherin on the cell surface*. Oncotarget, 2016. 7(51): p. 84030.
8. Caron, P. C., et al., *Murine and humanized constructs of monoclonal antibody M195 (anti-CD33) for the therapy of acute myelogenous leukemia*. Cancer, 1994. 73(S3): p. 1049-1056.
9. Taborda, C. P., et al., *More is not necessarily better: prozone-like effects in passive immunization with IgG*. The Journal of Immunology, 2003. 170(7): p. 3621-3630.
10. Habiel, D. M., et al., *Modeling idiopathic pulmonary fibrosis in humanized severe combined immunodeficient mice*. The American journal of pathology, 2018. 188(4): p. 891-903.
11. Elrick, L. J., et al., *Generation of a monoclonal human single chain antibody fragment to hepatic stellate cells—a potential mechanism for targeting liver anti-fibrotic therapeutics*. Journal of hepatology, 2005. 42(6): p. 888-896.
12. Poelstra, K. and D. Schuppan, *Targeted therapy of liver fibrosis/cirrhosis and its complications*. Journal of hepatology, 2011. 55(3): p. 726-728.
13. Hmiel, L. K., K. A. Brorson, and M. T. Boyne, *Post-translational structural modifications of immunoglobulin G and their effect on biological activity*. Analytical and bioanalytical chemistry, 2015. 407(1): p. 79-94.
14. Asmani, M., et al., *Fibrotic microtissue array to predict anti-fibrosis drug efficacy*. Nature communications, 2018. 9(1): p. 2066.

Table of Sequences

| SEQ ID NO | Clone Name | Length | Type |
|---|---|---|---|
| 1 | A10A HEAVY | 402 | DNA |
| 2 | A10A LIGHT | 384 | DNA |
| 3 | 19D8 HEAVY | 417 | DNA |

Table of Sequences

| SEQ ID NO | Clone Name | Length | Type |
|---|---|---|---|
| 4 | 19D8 LIGHT | 381 | DNA |
| 5 | A10A CDR1 (H) | 15 | DNA |
| 6 | A10A CDR2 (H) | 51 | DNA |
| 7 | A10A CDR3 (H) | 18 | DNA |
| 8 | A10A CDR1 (L) | 30 | DNA |
| 9 | A10A CDR2 (L) | 21 | DNA |
| 10 | A10A CDR3 (L) | 27 | DNA |
| 11 | 19D8 CDR1 (H) | 15 | DNA |
| 12 | 19D8 CDR2 (H) | 48 | DNA |
| 13 | 19D8 CDR3 (H) | 36 | DNA |
| 14 | 19D8 CDR1 (L) | 33 | DNA |
| 15 | 19D8 CDR2 (L) | 21 | DNA |
| 16 | 19D8 CDR2 (L) | 27 | DNA |
| 17 | PRODOMAIN | 68 | Protein |
| 18 | A10A HEAVY | 134 | Protein |
| 19 | A10A LIGHT | 128 | Protein |
| 20 | 19D8 HEAVY | 139 | Protein |
| 21 | 19D8 LIGHT | 127 | Protein |
| 22 | A10A CDR1 (H) | 5 | Protein |
| 23 | A10A CDR2 (H) | 17 | Protein |
| 24 | A10A CDR3 (H) | 6 | Protein |
| 25 | A10A CDR1 (L) | 10 | Protein |
| 26 | A10A CDR2 (L) | 7 | Protein |
| 27 | A10A CDR3 (L) | 9 | Protein |
| 28 | 19D8 CDR1 (H) | 5 | Protein |
| 29 | 19D8 CDR2 (H) | 16 | Protein |
| 30 | 19D8 CDR3 (H) | 12 | Protein |
| 31 | 19D8 CDR1 (L) | 11 | Protein |
| 32 | 19D8 CDR2 (L) | 7 | Protein |
| 33 | 19D8 CDR3 (L) | 9 | Protein |
| 34 | A10A HC0 | 461 | Protein |
| 35 | A10A HC1 | 461 | Protein |
| 36 | A10A HC2 | 461 | Protein |
| 37 | A10A HC3 | 461 | Protein |
| 38 | A10A HC4 | 461 | Protein |
| 39 | A10A HC5 | 461 | Protein |
| 40 | A10A LC0 | 233 | Protein |
| 41 | A10A LC1 | 233 | Protein |
| 42 | A10A LC2 | 233 | Protein |
| 43 | A10A LC3 | 233 | Protein |
| 44 | A10A LC4 | 233 | Protein |
| 45 | A10A LC5 | 233 | Protein |
| 46 | 19D8 HC0 | 469 | Protein |
| 47 | 19D8 HC1 | 469 | Protein |
| 48 | 19D8 HC2 | 469 | Protein |
| 49 | 19D8 HC3 | 468 | Protein |
| 50 | 19D8 HC4 | 469 | Protein |
| 51 | 19D8 HC5 | 469 | Protein |
| 52 | 19D8 LC0 | 234 | Protein |
| 53 | 19D8 LC1 | 234 | Protein |
| 54 | 19D8 LC2 | 234 | Protein |
| 55 | 19D8 LC3 | 234 | Protein |
| 56 | 19D8 LC4 | 234 | Protein |
| 57 | 19D8LC5 | 234 | Protein |

We claim:

1. A humanized antibody which specifically binds to pro-N-cadherin in its pro-domain, said humanized antibody comprising:
    framework portions of a human antibody; and
    six complementarity determining regions (CDRs) of a mouse antibody, wherein the CDRs are SEQ ID NO: 22-27 or SEQ ID NO: 28-33.

2. The humanized antibody of claim 1 wherein the human antibody is an antibody isotype selected from the group consisting of IgG1, IgG2, IgG3, and IgG4.

3. The humanized antibody of claim 1 wherein the humanized antibody is conjugated to a cytotoxic moiety.

4. The humanized antibody of claim 3 wherein the cytotoxic moiety is selected from the group consisting of a chemotherapeutic drug, a toxin, and a radioisotope.

5. A method of treating a human with a pathological fibrotic condition to reduce number of pathological fibrotic cells in the human, said method comprising: administering to the human a humanized antibody that binds to pro-N-cadherin in its pro-domain, whereby number of pathological fibrotic cells is reduced; wherein the humanized antibody comprises framework portions from a human antibody; and six complementarity determining regions (CDRs) from a mouse antibody, wherein the CDRs are SEQ ID NO: 22-27 or SEQ ID NO: 28-33.

6. The method of claim 5 wherein the pathological fibrotic condition is a disease of an organ selected from the group consisting of heart, lung, skin, kidney, and liver.

7. The method of claim 5 wherein the pathological fibrotic condition is selected from the group consisting of pulmonary fibrosis, radiation-induced lung injury, cystic fibrosis, idiopathic pulmonary fibrosis, liver cirrhosis, atrial fibrosis, and endomyocardial fibrosis.

8. The method of claim 5 wherein the pathological fibrotic condition is selected from the group consisting of scleroderma, Crohn's disease, and arthrofibrosis.

9. A method of treating a human with a tumor condition to reduce number of tumor cells in the human, said method comprising: administering to the human a humanized antibody that binds to pro-N-cadherin in its pro-domain, whereby number of tumor cells in the human is reduced; wherein the humanized antibody comprises framework portions from a human antibody and six complementarity determining regions (CDRs) from a mouse antibody; and wherein the CDRs are SEQ ID NO: 22-27 or SEQ ID NO: 28-33.

10. A chimeric antibody which specifically binds to pro-N-cadherin in its pro-domain, said chimeric antibody comprising:
    framework portions from a non-murine antibody; and six complementarity determining regions (CDRs) from a mouse antibody, wherein the CDRs are SEQ ID NO: 22-27 or SEQ ID NO: 28-33.

11. The chimeric antibody of claim 10 wherein the framework portions comprise up to 10 amino acid residue substitutions relative to the non-murine antibody.

12. The chimeric antibody of claim 10 that comprises heavy and light chain variable regions comprising SEQ ID NO: 18-19 or 20-21.

13. The chimeric antibody of claim 10 that has an affinity for pro-N-cadherin that is at least as great as that of a murine antibody comprising the same six CDRs.

14. The chimeric antibody of claim 10 that as an affinity for pro-N-cadherin that is at least two times as great as that of a murine antibody comprising the same six CDRs.

* * * * *

SEQUENCE LISTING

<160> NUMBER OF SEQ ID NOS: 57

<210> SEQ ID NO 1
<211> LENGTH: 402
<212> TYPE: DNA
<213> ORGANISM: Mus musculus

<400> SEQUENCE: 1

```
atggaatgga gttggatatt tctctttctc ctgtcaggaa ctgcaggtgt ccactctgag    60
gtccagctgc agcagtctgg acctgagctg gtaaagcctg gggcttcagt gaagatgtcc   120
tgcaaggctt ctggatacac attcactagc tatcttatgc actgggtgaa gcagaagcct   180
gggcagggcc ttgagtggat tggatatatt aatccttata ttgatgtaac taaatacaat   240
gagaagttca aggcaaggc cacactgact tcagacaaat cctccagcac agccttcatg   300
gagctcagca gcctgacctc tgaggactct gcggtctatt actgtgcggg gggggactac   360
gaggactact ggggccaagg caccactctc acagtctcct ca                      402
```

<210> SEQ ID NO 2
<211> LENGTH: 384
<212> TYPE: DNA
<213> ORGANISM: Mus musculus

<400> SEQUENCE: 2

```
atggattctc aggtgcagat tttcagcttc ctgctaatca gtatctcagt tgtaatgtcc    60
agaggagaaa atgtgctcac ccagtctcca gcaatcatgt ctgcatctct aggggagaag   120
gtcaccatga gctgcagggc cagctcaagt gtaaattaca tgtactggta ccagcagaag   180
tcagatgcct cccccaaact atggatttat acacatccaa cctggctccc ggagtcccca   240
gatcgcttca gtggcagtgg gtctgggaac tcttattctc tcacaatcag cagcatggag   300
```

```
ggtgaagatg ctgccactta ttattgccag cagtttagta gtcccccatt cacgttcggc    360
tcggggacaa agttggaaat aaaa                                           384

<210> SEQ ID NO 3
<211> LENGTH: 417
<212> TYPE: DNA
<213> ORGANISM: Mus musculus

<400> SEQUENCE: 3
atgaacttcg ggttcagctt gattttcctt gtccttgttt taaaaggtgt ccagtgtgaa     60
gtgaaactgg tggagtctgg gggaggctta gtgaacctg gagggtccct gaaactctcc    120
tgtgcagcct ctgcattcac tttcagtact tatgccatgt cttgggttcg ccagactcca   180
gagaagaggc tggagtgggt cacatccatt agtagtggtg gtagaaccta ctatccagac   240
agtgtgaagg gccgattcaa catctccaga gataatgcca ggaacatcct gtacctgcaa   300
atgagcactc tgaggtctga ggacacggcc atgtattact gtgcaagatc ctatggtaac   360
tacgtcggct atgttatgga ctactggggt caaggaacct cagtcaccgt ctcctca      417

<210> SEQ ID NO 4
<211> LENGTH: 381
<212> TYPE: DNA
<213> ORGANISM: Mus musculus

<400> SEQUENCE: 4
atgcgtgtgc ccactcaggt cctggggttg ctgctgctgt ggcttacagg tgccagatgt     60
gacatccaaa tgactcagtc tccagcctcc tatctgcat ctgtgggaga aactgtcacc    120
atcacatgtc gagcaagtga caatatttac agttattttg catggtatcg gcagaaacag   180
ggaaattctc ctcagctcct ggtctataat gcaaaaacct tagcagaagg tgtgccgtca   240
aggttcagtg gcagtggatc aggcacacac ttttctctaa agatcaataa cctgcagcct   300
gaggattttg ggacttatta ctgtcaacat cattatggtc tccgtggac gttcggtgga   360 ggcaccaagc tggaaatcaa a                                              381

<210> SEQ ID NO 5
<211> LENGTH: 15
<212> TYPE: DNA
<213> ORGANISM: Mus musculus

<400> SEQUENCE: 5
agctatctta tgcac                                                      15

<210> SEQ ID NO 6
<211> LENGTH: 51
<212> TYPE: DNA
<213> ORGANISM: Mus musculus

<400> SEQUENCE: 6
tatattaatc cttatattga tgtaactaaa tacaatgaga agttcaaagg c               51

<210> SEQ ID NO 7
<211> LENGTH: 18
<212> TYPE: DNA
<213> ORGANISM: Mus musculus

<400> SEQUENCE: 7
ggggactacg aggactac                                                   18
```

```
<210> SEQ ID NO 8
<211> LENGTH: 30
<212> TYPE: DNA
<213> ORGANISM: Mus musculus

<400> SEQUENCE: 8
agggccagct caagtgtaaa ttacatgtac                                    30

<210> SEQ ID NO 9
<211> LENGTH: 21
<212> TYPE: DNA
<213> ORGANISM: Mus musculus

<400> SEQUENCE: 9
tacacatcca acctggctcc c                                             21

<210> SEQ ID NO 10
<211> LENGTH: 27
<212> TYPE: DNA
<213> ORGANISM: Mus musculus

<400> SEQUENCE: 10
cagcagttta gtagtccccc attcacg                                       27

<210> SEQ ID NO 11
<211> LENGTH: 15
<212> TYPE: DNA
<213> ORGANISM: Mus musculus

<400> SEQUENCE: 11
acttatgcca tgtct                                                    15

<210> SEQ ID NO 12
<211> LENGTH: 48
<212> TYPE: DNA
<213> ORGANISM: Mus musculus

<400> SEQUENCE: 12
tccattagta gtggtggtag aacctactat ccagacagtg tgaagggc                48

<210> SEQ ID NO 13
<211> LENGTH: 36
<212> TYPE: DNA
<213> ORGANISM: Mus musculus

<400> SEQUENCE: 13
tcctatggta actacgtcgg ctatgttatg gactac                             36

<210> SEQ ID NO 14
<211> LENGTH: 33
<212> TYPE: DNA
<213> ORGANISM: Mus musculus

<400> SEQUENCE: 14
cgagcaagtg acaatattta cagttatttt gca                                33

<210> SEQ ID NO 15
<211> LENGTH: 21
<212> TYPE: DNA
<213> ORGANISM: Mus musculus

<400> SEQUENCE: 15
aatgcaaaaa ccttagcaga a                                             21
```

<210> SEQ ID NO 16
<211> LENGTH: 27
<212> TYPE: DNA
<213> ORGANISM: Mus musculus

<400> SEQUENCE: 16
caacatcatt atggtcctcc gtggacg                                27

<210> SEQ ID NO 17
<211> LENGTH: 68
<212> TYPE: PRT
<213> ORGANISM: Homo sapiens

<400> SEQUENCE: 17

Phe Pro Leu Ser Ser Glu His Ala Lys Phe Leu Ile Tyr Ala Gln Asp
1               5                   10                  15

Lys Glu Thr Gln Glu Lys Trp Gln Val Ala Val Lys Leu Ser Leu Lys
                20                  25                  30

Pro Thr Leu Thr Glu Glu Ser Val Lys Glu Ser Ala Glu Val Glu Glu
            35                  40                  45

Ile Val Phe Pro Arg Gln Phe Ser Lys His Ser Gly His Leu Gln Arg
    50                  55                  60

Gln Lys Arg Asp
65

<210> SEQ ID NO 18
<211> LENGTH: 134
<212> TYPE: PRT
<213> ORGANISM: Mus musculus

<400> SEQUENCE: 18

Met Glu Trp Ser Trp Ile Phe Leu Phe Leu Leu Ser Gly Thr Ala Gly
1               5                   10                  15

Val His Ser Glu Val Gln Leu Gln Gln Ser Gly Pro Glu Leu Val Lys
                20                  25                  30

Pro Gly Ala Ser Val Lys Met Ser Cys Lys Ala Ser Gly Tyr Thr Phe
            35                  40                  45

Thr Ser Tyr Leu Met His Trp Val Lys Gln Lys Pro Gly Gln Gly Leu
    50                  55                  60

Glu Trp Ile Gly Tyr Ile Asn Pro Tyr Ile Asp Val Thr Lys Tyr Asn
65                  70                  75                  80

Glu Lys Phe Lys Gly Lys Ala Thr Leu Thr Ser Asp Lys Ser Ser Ser
                85                  90                  95

Thr Ala Phe Met Glu Leu Ser Ser Leu Thr Ser Glu Asp Ser Ala Val
            100                 105                 110

Tyr Tyr Cys Ala Gly Gly Asp Tyr Glu Asp Tyr Trp Gly Gln Gly Thr
        115                 120                 125

Thr Leu Thr Val Ser Ser
        130

<210> SEQ ID NO 19
<211> LENGTH: 128
<212> TYPE: PRT
<213> ORGANISM: Mus musculus

<400> SEQUENCE: 19

Met Asp Ser Gln Val Gln Ile Phe Ser Phe Leu Leu Ile Ser Ile Ser
1               5                   10                  15

```
Val Val Met Ser Arg Gly Glu Asn Val Leu Thr Gln Ser Pro Ala Ile
                20                  25                  30

Met Ser Ala Ser Leu Gly Glu Lys Val Thr Met Ser Cys Arg Ala Ser
            35                  40                  45

Ser Ser Val Asn Tyr Met Tyr Trp Tyr Gln Gln Lys Ser Asp Ala Ser
        50                  55                  60

Pro Lys Leu Trp Ile Tyr Tyr Thr Ser Asn Leu Ala Pro Gly Val Pro
65                  70                  75                  80

Asp Arg Phe Ser Gly Ser Gly Ser Gly Asn Ser Tyr Ser Leu Thr Ile
                85                  90                  95

Ser Ser Met Glu Gly Glu Asp Ala Ala Thr Tyr Tyr Cys Gln Gln Phe
            100                 105                 110

Ser Ser Pro Pro Phe Thr Phe Gly Ser Gly Thr Lys Leu Glu Ile Lys
        115                 120                 125

<210> SEQ ID NO 20
<211> LENGTH: 139
<212> TYPE: PRT
<213> ORGANISM: Mus musculus

<400> SEQUENCE: 20

Met Asn Phe Gly Phe Ser Leu Ile Phe Leu Val Leu Val Leu Lys Gly
1               5                   10                  15

Val Gln Cys Glu Val Lys Leu Val Glu Ser Gly Gly Gly Leu Val Asn
                20                  25                  30

Pro Gly Gly Ser Leu Lys Leu Ser Cys Ala Ala Ser Ala Phe Thr Phe
            35                  40                  45

Ser Thr Tyr Ala Met Ser Trp Val Arg Gln Thr Pro Glu Lys Arg Leu
        50                  55                  60

Glu Trp Val Thr Ser Ile Ser Ser Gly Gly Arg Thr Tyr Tyr Pro Asp
65                  70                  75                  80

Ser Val Lys Gly Arg Phe Asn Ile Ser Arg Asp Asn Ala Arg Asn Ile
                85                  90                  95

Leu Tyr Leu Gln Met Ser Thr Leu Arg Ser Glu Asp Thr Ala Met Tyr
            100                 105                 110

Tyr Cys Ala Arg Ser Tyr Gly Asn Tyr Val Gly Tyr Val Met Asp Tyr
        115                 120                 125

Trp Gly Gln Gly Thr Ser Val Thr Val Ser Ser
            130                 135

<210> SEQ ID NO 21
<211> LENGTH: 127
<212> TYPE: PRT
<213> ORGANISM: Mus musculus

<400> SEQUENCE: 21

Met Arg Val Pro Thr Gln Val Leu Gly Leu Leu Leu Leu Trp Leu Thr
1               5                   10                  15

Gly Ala Arg Cys Asp Ile Gln Met Thr Gln Ser Pro Ala Ser Leu Ser
                20                  25                  30

Ala Ser Val Gly Glu Thr Val Thr Ile Thr Cys Arg Ala Ser Asp Asn
            35                  40                  45

Ile Tyr Ser Tyr Phe Ala Trp Tyr Arg Gln Lys Gln Gly Asn Ser Pro
        50                  55                  60

Gln Leu Leu Val Tyr Asn Ala Lys Thr Leu Ala Glu Gly Val Pro Ser
65                  70                  75                  80
```

```
Arg Phe Ser Gly Ser Gly Ser Gly Thr His Phe Ser Leu Lys Ile Asn
                85                  90                  95

Asn Leu Gln Pro Glu Asp Phe Gly Thr Tyr Tyr Cys Gln His His Tyr
            100                 105                 110

Gly Pro Pro Trp Thr Phe Gly Gly Gly Thr Lys Leu Glu Ile Lys
        115                 120                 125

<210> SEQ ID NO 22
<211> LENGTH: 5
<212> TYPE: PRT
<213> ORGANISM: Mus musculus

<400> SEQUENCE: 22

Ser Tyr Leu Met His
1               5

<210> SEQ ID NO 23
<211> LENGTH: 17
<212> TYPE: PRT
<213> ORGANISM: Mus musculus

<400> SEQUENCE: 23

Tyr Ile Asn Pro Tyr Ile Asp Val Thr Lys Tyr Asn Glu Lys Phe Lys
1               5                   10                  15

Gly

<210> SEQ ID NO 24
<211> LENGTH: 6
<212> TYPE: PRT
<213> ORGANISM: Mus musculus

<400> SEQUENCE: 24

Gly Asp Tyr Glu Asp Tyr
1               5

<210> SEQ ID NO 25
<211> LENGTH: 10
<212> TYPE: PRT
<213> ORGANISM: Mus musculus

<400> SEQUENCE: 25

Arg Ala Ser Ser Val Asn Tyr Met Tyr
1               5                   10

<210> SEQ ID NO 26
<211> LENGTH: 7
<212> TYPE: PRT
<213> ORGANISM: Mus musculus

<400> SEQUENCE: 26

Tyr Thr Ser Asn Leu Ala Pro
1               5

<210> SEQ ID NO 27
<211> LENGTH: 9
<212> TYPE: PRT
<213> ORGANISM: Mus musculus

<400> SEQUENCE: 27

Gln Gln Phe Ser Ser Pro Pro Phe Thr
1               5

<210> SEQ ID NO 28
```

```
<211> LENGTH: 5
<212> TYPE: PRT
<213> ORGANISM: Mus musculus

<400> SEQUENCE: 28

Thr Tyr Ala Met Ser
1               5

<210> SEQ ID NO 29
<211> LENGTH: 16
<212> TYPE: PRT
<213> ORGANISM: Mus musculus

<400> SEQUENCE: 29

Ser Ile Ser Ser Gly Gly Arg Thr Tyr Tyr Pro Asp Ser Val Lys Gly
1               5                   10                  15

<210> SEQ ID NO 30
<211> LENGTH: 12
<212> TYPE: PRT
<213> ORGANISM: Mus musculus

<400> SEQUENCE: 30

Ser Tyr Gly Asn Tyr Val Gly Tyr Val Met Asp Tyr
1               5                   10

<210> SEQ ID NO 31
<211> LENGTH: 11
<212> TYPE: PRT
<213> ORGANISM: Mus musculus

<400> SEQUENCE: 31

Arg Ala Ser Asp Asn Ile Tyr Ser Tyr Phe Ala
1               5                   10

<210> SEQ ID NO 32
<211> LENGTH: 7
<212> TYPE: PRT
<213> ORGANISM: Mus musculus

<400> SEQUENCE: 32

Asn Ala Lys Thr Leu Ala Glu
1               5

<210> SEQ ID NO 33
<211> LENGTH: 9
<212> TYPE: PRT
<213> ORGANISM: Mus musculus

<400> SEQUENCE: 33

Gln His His Tyr Gly Pro Pro Trp Thr
1               5

<210> SEQ ID NO 34
<211> LENGTH: 461
<212> TYPE: PRT
<213> ORGANISM: Artificial Sequence
<220> FEATURE:
<223> OTHER INFORMATION: chimeric antibody molecules

<400> SEQUENCE: 34

Met Gly Trp Thr Leu Val Phe Leu Phe Leu Leu Ser Val Thr Ala Gly
1               5                   10                  15

Val His Ser Glu Val Gln Leu Gln Gln Ser Gly Pro Glu Leu Val Lys
                20                  25                  30
```

Pro Gly Ala Ser Val Lys Met Ser Cys Lys Ala Ser Gly Tyr Thr Phe
            35                  40                  45

Thr Ser Tyr Leu Met His Trp Val Lys Gln Lys Pro Gly Gln Gly Leu
        50                  55                  60

Glu Trp Ile Gly Tyr Ile Asn Pro Tyr Ile Asp Val Thr Lys Tyr Asn
65                  70                  75                  80

Glu Lys Phe Lys Gly Lys Ala Thr Leu Thr Ser Asp Lys Ser Ser Ser
                85                  90                  95

Thr Ala Phe Met Glu Leu Ser Ser Leu Thr Ser Glu Asp Ser Ala Val
            100                 105                 110

Tyr Tyr Cys Ala Gly Gly Asp Tyr Glu Asp Tyr Trp Gly Gln Gly Thr
        115                 120                 125

Thr Leu Thr Val Ser Ser Ala Ser Thr Lys Gly Pro Ser Val Phe Pro
    130                 135                 140

Leu Ala Pro Cys Ser Arg Ser Thr Ser Glu Ser Thr Ala Ala Leu Gly
145                 150                 155                 160

Cys Leu Val Lys Asp Tyr Phe Pro Glu Pro Val Thr Val Ser Trp Asn
                165                 170                 175

Ser Gly Ala Leu Thr Ser Gly Val His Thr Phe Pro Ala Val Leu Gln
            180                 185                 190

Ser Ser Gly Leu Tyr Ser Leu Ser Ser Val Val Thr Val Pro Ser Ser
        195                 200                 205

Ser Leu Gly Thr Lys Thr Tyr Thr Cys Asn Val Asp His Lys Pro Ser
    210                 215                 220

Asn Thr Lys Val Asp Lys Arg Val Glu Ser Lys Tyr Gly Pro Pro Cys
225                 230                 235                 240

Pro Pro Cys Pro Ala Pro Glu Phe Leu Gly Gly Pro Ser Val Phe Leu
                245                 250                 255

Phe Pro Pro Lys Pro Lys Asp Thr Leu Met Ile Ser Arg Thr Pro Glu
            260                 265                 270

Val Thr Cys Val Val Val Asp Val Ser Gln Glu Asp Pro Glu Val Gln
        275                 280                 285

Phe Asn Trp Tyr Val Asp Gly Val Glu Val His Asn Ala Lys Thr Lys
    290                 295                 300

Pro Arg Glu Glu Gln Phe Asn Ser Thr Tyr Arg Val Val Ser Val Leu
305                 310                 315                 320

Thr Val Leu His Gln Asp Trp Leu Asn Gly Lys Glu Tyr Lys Cys Lys
                325                 330                 335

Val Ser Asn Lys Gly Leu Pro Ser Ser Ile Glu Lys Thr Ile Ser Lys
            340                 345                 350

Ala Lys Gly Gln Pro Arg Glu Pro Gln Val Tyr Thr Leu Pro Pro Ser
        355                 360                 365

Gln Glu Glu Met Thr Lys Asn Gln Val Ser Leu Thr Cys Leu Val Lys
    370                 375                 380

Gly Phe Tyr Pro Ser Asp Ile Ala Val Glu Trp Glu Ser Asn Gly Gln
385                 390                 395                 400

Pro Glu Asn Asn Tyr Lys Thr Thr Pro Pro Val Leu Asp Ser Asp Gly
                405                 410                 415

Ser Phe Phe Leu Tyr Ser Arg Leu Thr Val Asp Lys Ser Arg Trp Gln
            420                 425                 430

Glu Gly Asn Val Phe Ser Cys Ser Val Met His Glu Ala Leu His Asn
        435                 440                 445

```
His Tyr Thr Gln Lys Ser Leu Ser Leu Ser Leu Gly Lys
    450                 455                 460
```

<210> SEQ ID NO 35
<211> LENGTH: 461
<212> TYPE: PRT
<213> ORGANISM: Artificial Sequence
<220> FEATURE:
<223> OTHER INFORMATION: chimeric antibody molecules

<400> SEQUENCE: 35

```
Met Gly Trp Thr Leu Val Phe Leu Phe Leu Leu Ser Val Thr Ala Gly
1               5                   10                  15

Val His Ser Glu Val Gln Leu Val Glu Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Ser Tyr Leu Met His Trp Val Arg Gln Ala Pro Gly Gln Gly Leu
    50                  55                  60

Glu Trp Met Gly Tyr Ile Asn Pro Tyr Ile Asp Val Thr Lys Tyr Asn
65                  70                  75                  80

Glu Lys Phe Lys Gly Arg Val Thr Met Thr Arg Asp Thr Ser Thr Ser
                85                  90                  95

Thr Val Tyr Met Glu Leu Ser Ser Leu Arg Ser Glu Asp Thr Ala Val
            100                 105                 110

Tyr Tyr Cys Ala Gly Gly Asp Tyr Glu Asp Tyr Trp Gly Gln Gly Thr
        115                 120                 125

Leu Val Thr Val Ser Ser Ala Ser Thr Lys Gly Pro Ser Val Phe Pro
    130                 135                 140

Leu Ala Pro Cys Ser Arg Ser Thr Ser Glu Ser Thr Ala Ala Leu Gly
145                 150                 155                 160

Cys Leu Val Lys Asp Tyr Phe Pro Glu Pro Val Thr Val Ser Trp Asn
                165                 170                 175

Ser Gly Ala Leu Thr Ser Gly Val His Thr Phe Pro Ala Val Leu Gln
            180                 185                 190

Ser Ser Gly Leu Tyr Ser Leu Ser Ser Val Val Thr Val Pro Ser Ser
        195                 200                 205

Ser Leu Gly Thr Lys Thr Tyr Thr Cys Asn Val Asp His Lys Pro Ser
    210                 215                 220

Asn Thr Lys Val Asp Lys Arg Val Glu Ser Lys Tyr Gly Pro Pro Cys
225                 230                 235                 240

Pro Pro Cys Pro Ala Pro Glu Phe Leu Gly Gly Pro Ser Val Phe Leu
                245                 250                 255

Phe Pro Pro Lys Pro Lys Asp Thr Leu Met Ile Ser Arg Thr Pro Glu
            260                 265                 270

Val Thr Cys Val Val Val Asp Val Ser Gln Glu Asp Pro Glu Val Gln
        275                 280                 285

Phe Asn Trp Tyr Val Asp Gly Val Glu Val His Asn Ala Lys Thr Lys
    290                 295                 300

Pro Arg Glu Glu Gln Phe Asn Ser Thr Tyr Arg Val Val Ser Val Leu
305                 310                 315                 320

Thr Val Leu His Gln Asp Trp Leu Asn Gly Lys Glu Tyr Lys Cys Lys
                325                 330                 335

Val Ser Asn Lys Gly Leu Pro Ser Ser Ile Glu Lys Thr Ile Ser Lys
            340                 345                 350
```

```
Ala Lys Gly Gln Pro Arg Glu Pro Gln Val Tyr Thr Leu Pro Pro Ser
            355                 360                 365

Gln Glu Glu Met Thr Lys Asn Gln Val Ser Leu Thr Cys Leu Val Lys
    370                 375                 380

Gly Phe Tyr Pro Ser Asp Ile Ala Val Glu Trp Glu Ser Asn Gly Gln
385                 390                 395                 400

Pro Glu Asn Asn Tyr Lys Thr Thr Pro Pro Val Leu Asp Ser Asp Gly
                405                 410                 415

Ser Phe Phe Leu Tyr Ser Arg Leu Thr Val Asp Lys Ser Arg Trp Gln
                420                 425                 430

Glu Gly Asn Val Phe Ser Cys Ser Val Met His Glu Ala Leu His Asn
            435                 440                 445

His Tyr Thr Gln Lys Ser Leu Ser Leu Ser Leu Gly Lys
    450                 455                 460

<210> SEQ ID NO 36
<211> LENGTH: 461
<212> TYPE: PRT
<213> ORGANISM: Artificial Sequence
<220> FEATURE:
<223> OTHER INFORMATION: chimeric antibody molecules

<400> SEQUENCE: 36

Met Gly Trp Thr Leu Val Phe Leu Phe Leu Leu Ser Val Thr Ala Gly
1               5                   10                  15

Val His Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Ser Tyr Leu Met His Trp Val Arg Gln Ala Pro Gly Gln Arg Leu
    50                  55                  60

Glu Trp Ile Gly Tyr Ile Asn Pro Tyr Ile Asp Val Thr Lys Tyr Asn
65                  70                  75                  80

Glu Lys Phe Lys Gly Arg Val Thr Ile Thr Arg Asp Thr Ser Ala Ser
                85                  90                  95

Thr Ala Tyr Met Glu Leu Ser Ser Leu Arg Ser Glu Asp Thr Ala Val
            100                 105                 110

Tyr Tyr Cys Ala Gly Gly Asp Tyr Glu Asp Tyr Trp Gly Gln Gly Thr
        115                 120                 125

Leu Val Thr Val Ser Ser Ala Ser Thr Lys Gly Pro Ser Val Phe Pro
    130                 135                 140

Leu Ala Pro Cys Ser Arg Ser Thr Ser Glu Ser Thr Ala Ala Leu Gly
145                 150                 155                 160

Cys Leu Val Lys Asp Tyr Phe Pro Glu Pro Val Thr Val Ser Trp Asn
                165                 170                 175

Ser Gly Ala Leu Thr Ser Gly Val His Thr Phe Pro Ala Val Leu Gln
            180                 185                 190

Ser Ser Gly Leu Tyr Ser Leu Ser Ser Val Val Thr Val Pro Ser Ser
        195                 200                 205

Ser Leu Gly Thr Lys Thr Tyr Thr Cys Asn Val Asp His Lys Pro Ser
    210                 215                 220

Asn Thr Lys Val Asp Lys Arg Val Glu Ser Lys Tyr Gly Pro Pro Cys
225                 230                 235                 240

Pro Pro Cys Pro Ala Pro Glu Phe Leu Gly Gly Pro Ser Val Phe Leu
                245                 250                 255
```

Phe Pro Pro Lys Pro Lys Asp Thr Leu Met Ile Ser Arg Thr Pro Glu
            260                 265                 270

Val Thr Cys Val Val Val Asp Val Ser Gln Glu Asp Pro Glu Val Gln
        275                 280                 285

Phe Asn Trp Tyr Val Asp Gly Val Glu Val His Asn Ala Lys Thr Lys
    290                 295                 300

Pro Arg Glu Glu Gln Phe Asn Ser Thr Tyr Arg Val Val Ser Val Leu
305                 310                 315                 320

Thr Val Leu His Gln Asp Trp Leu Asn Gly Lys Glu Tyr Lys Cys Lys
                325                 330                 335

Val Ser Asn Lys Gly Leu Pro Ser Ser Ile Glu Lys Thr Ile Ser Lys
            340                 345                 350

Ala Lys Gly Gln Pro Arg Glu Pro Gln Val Tyr Thr Leu Pro Pro Ser
        355                 360                 365

Gln Glu Glu Met Thr Lys Asn Gln Val Ser Leu Thr Cys Leu Val Lys
    370                 375                 380

Gly Phe Tyr Pro Ser Asp Ile Ala Val Glu Trp Glu Ser Asn Gly Gln
385                 390                 395                 400

Pro Glu Asn Asn Tyr Lys Thr Thr Pro Pro Val Leu Asp Ser Asp Gly
                405                 410                 415

Ser Phe Phe Leu Tyr Ser Arg Leu Thr Val Asp Lys Ser Arg Trp Gln
            420                 425                 430

Glu Gly Asn Val Phe Ser Cys Ser Val Met His Glu Ala Leu His Asn
        435                 440                 445

His Tyr Thr Gln Lys Ser Leu Ser Leu Ser Leu Gly Lys
    450                 455                 460

<210> SEQ ID NO 37
<211> LENGTH: 461
<212> TYPE: PRT
<213> ORGANISM: Artificial Sequence
<220> FEATURE:
<223> OTHER INFORMATION: chimeric antibody molecules

<400> SEQUENCE: 37

Met Gly Trp Thr Leu Val Phe Leu Phe Leu Leu Ser Val Thr Ala Gly
1               5                   10                  15

Val His Ser Gln Val Gln Leu Val Gln Ser Gly Ala Glu Val Thr Lys
            20                  25                  30

Pro Gly Ala Ser Val Lys Val Ser Cys Lys Ala Ser Gly Tyr Thr Phe
        35                  40                  45

Thr Ser Tyr Leu Met His Trp Val Arg Gln Ala Pro Gly Gln Gly Leu
    50                  55                  60

Glu Trp Val Gly Tyr Ile Asn Pro Tyr Ile Asp Val Thr Lys Tyr Asn
65                  70                  75                  80

Glu Lys Phe Lys Gly Arg Val Thr Leu Thr Arg Asp Thr Ser Thr Thr
                85                  90                  95

Thr Val Tyr Met Glu Leu Ser Ser Leu Arg Ser Glu Asp Thr Ala Val
            100                 105                 110

Tyr Tyr Cys Ala Gly Gly Asp Tyr Glu Asp Tyr Trp Gly Gln Gly Thr
        115                 120                 125

Thr Val Thr Val Ser Ser Ala Ser Thr Lys Gly Pro Ser Val Phe Pro
    130                 135                 140

Leu Ala Pro Cys Ser Arg Ser Thr Ser Glu Ser Thr Ala Ala Leu Gly
145                 150                 155                 160

Cys Leu Val Lys Asp Tyr Phe Pro Glu Pro Val Thr Val Ser Trp Asn
            165                 170                 175

Ser Gly Ala Leu Thr Ser Gly Val His Thr Phe Pro Ala Val Leu Gln
            180                 185                 190

Ser Ser Gly Leu Tyr Ser Leu Ser Ser Val Val Thr Val Pro Ser Ser
            195                 200                 205

Ser Leu Gly Thr Lys Thr Tyr Thr Cys Asn Val Asp His Lys Pro Ser
            210                 215                 220

Asn Thr Lys Val Asp Lys Arg Val Glu Ser Lys Tyr Gly Pro Pro Cys
225                 230                 235                 240

Pro Pro Cys Pro Ala Pro Glu Phe Leu Gly Gly Pro Ser Val Phe Leu
                245                 250                 255

Phe Pro Pro Lys Pro Lys Asp Thr Leu Met Ile Ser Arg Thr Pro Glu
            260                 265                 270

Val Thr Cys Val Val Val Asp Val Ser Gln Glu Asp Pro Glu Val Gln
            275                 280                 285

Phe Asn Trp Tyr Val Asp Gly Val Glu Val His Asn Ala Lys Thr Lys
            290                 295                 300

Pro Arg Glu Glu Gln Phe Asn Ser Thr Tyr Arg Val Val Ser Val Leu
305                 310                 315                 320

Thr Val Leu His Gln Asp Trp Leu Asn Gly Lys Glu Tyr Lys Cys Lys
                325                 330                 335

Val Ser Asn Lys Gly Leu Pro Ser Ser Ile Glu Lys Thr Ile Ser Lys
            340                 345                 350

Ala Lys Gly Gln Pro Arg Glu Pro Gln Val Tyr Thr Leu Pro Pro Ser
            355                 360                 365

Gln Glu Glu Met Thr Lys Asn Gln Val Ser Leu Thr Cys Leu Val Lys
            370                 375                 380

Gly Phe Tyr Pro Ser Asp Ile Ala Val Glu Trp Glu Ser Asn Gly Gln
385                 390                 395                 400

Pro Glu Asn Asn Tyr Lys Thr Thr Pro Pro Val Leu Asp Ser Asp Gly
                405                 410                 415

Ser Phe Phe Leu Tyr Ser Arg Leu Thr Val Asp Lys Ser Arg Trp Gln
            420                 425                 430

Glu Gly Asn Val Phe Ser Cys Ser Val Met His Glu Ala Leu His Asn
            435                 440                 445

His Tyr Thr Gln Lys Ser Leu Ser Leu Ser Leu Gly Lys
            450                 455                 460

<210> SEQ ID NO 38
<211> LENGTH: 461
<212> TYPE: PRT
<213> ORGANISM: Artificial Sequence
<220> FEATURE:
<223> OTHER INFORMATION: chimeric antibody molecules

<400> SEQUENCE: 38

Met Gly Trp Thr Leu Val Phe Leu Phe Leu Leu Ser Val Thr Ala Gly
1               5                   10                  15

Val His Ser Gln Val Gln Leu Val Gln Ser Gly Ala Glu Val Lys Lys
            20                  25                  30

Pro Gly Ala Ser Val Gln Val Ser Cys Lys Ala Ser Gly Tyr Thr Phe
            35                  40                  45

Thr Ser Tyr Leu Met His Trp Leu Arg Gln Ala Pro Gly Gln Gly Leu
        50                  55                  60

```
Glu Trp Met Gly Tyr Ile Asn Pro Tyr Ile Asp Val Thr Lys Tyr Asn
 65                  70                  75                  80
Glu Lys Phe Lys Gly Arg Val Thr Met Thr Ser Asp Thr Ser Ile Ser
                 85                  90                  95
Thr Ala Tyr Met Glu Leu Ser Ser Leu Arg Ser Asp Asp Thr Ala Val
            100                 105                 110
Tyr Tyr Cys Ala Gly Asp Tyr Glu Asp Tyr Trp Gly Gln Ala Thr
        115                 120                 125
Leu Val Thr Val Ser Ser Ala Ser Thr Lys Gly Pro Ser Val Phe Pro
    130                 135                 140
Leu Ala Pro Cys Ser Arg Ser Thr Ser Glu Ser Thr Ala Ala Leu Gly
145                 150                 155                 160
Cys Leu Val Lys Asp Tyr Phe Pro Glu Pro Val Thr Val Ser Trp Asn
                165                 170                 175
Ser Gly Ala Leu Thr Ser Gly Val His Thr Phe Pro Ala Val Leu Gln
            180                 185                 190
Ser Ser Gly Leu Tyr Ser Leu Ser Ser Val Val Thr Val Pro Ser Ser
        195                 200                 205
Ser Leu Gly Thr Lys Thr Tyr Thr Cys Asn Val Asp His Lys Pro Ser
    210                 215                 220
Asn Thr Lys Val Asp Lys Arg Val Glu Ser Lys Tyr Gly Pro Pro Cys
225                 230                 235                 240
Pro Pro Cys Pro Ala Pro Glu Phe Leu Gly Gly Pro Ser Val Phe Leu
                245                 250                 255
Phe Pro Pro Lys Pro Lys Asp Thr Leu Met Ile Ser Arg Thr Pro Glu
            260                 265                 270
Val Thr Cys Val Val Val Asp Val Ser Gln Glu Asp Pro Glu Val Gln
        275                 280                 285
Phe Asn Trp Tyr Val Asp Gly Val Glu Val His Asn Ala Lys Thr Lys
    290                 295                 300
Pro Arg Glu Glu Gln Phe Asn Ser Thr Tyr Arg Val Val Ser Val Leu
305                 310                 315                 320
Thr Val Leu His Gln Asp Trp Leu Asn Gly Lys Glu Tyr Lys Cys Lys
                325                 330                 335
Val Ser Asn Lys Gly Leu Pro Ser Ser Ile Glu Lys Thr Ile Ser Lys
            340                 345                 350
Ala Lys Gly Gln Pro Arg Glu Pro Gln Val Tyr Thr Leu Pro Pro Ser
        355                 360                 365
Gln Glu Glu Met Thr Lys Asn Gln Val Ser Leu Thr Cys Leu Val Lys
    370                 375                 380
Gly Phe Tyr Pro Ser Asp Ile Ala Val Glu Trp Glu Ser Asn Gly Gln
385                 390                 395                 400
Pro Glu Asn Asn Tyr Lys Thr Thr Pro Pro Val Leu Asp Ser Asp Gly
                405                 410                 415
Ser Phe Phe Leu Tyr Ser Arg Leu Thr Val Asp Lys Ser Arg Trp Gln
            420                 425                 430
Glu Gly Asn Val Phe Ser Cys Ser Val Met His Glu Ala Leu His Asn
        435                 440                 445
His Tyr Thr Gln Lys Ser Leu Ser Leu Ser Leu Gly Lys
    450                 455                 460

<210> SEQ ID NO 39
<211> LENGTH: 461
<212> TYPE: PRT
```

<213> ORGANISM: Artificial Sequence
<220> FEATURE:
<223> OTHER INFORMATION: chimeric antibody molecules

<400> SEQUENCE: 39

Met Gly Trp Thr Leu Val Phe Leu Phe Leu Leu Ser Val Thr Ala Gly
1               5                   10                  15

Val His Ser Gln Val Gln Leu Val Gln Ser Gly Ala Glu Val Lys Lys
                20                  25                  30

Pro Gly Ala Ser Val Lys Val Ser Cys Lys Ala Ser Gly Tyr Thr Phe
            35                  40                  45

Thr Ser Tyr Leu Met His Trp Val Arg Gln Ala Pro Gly Gln Gly Leu
        50                  55                  60

Glu Trp Met Gly Tyr Ile Asn Pro Tyr Ile Asp Val Thr Lys Tyr Asn
65                  70                  75                  80

Glu Lys Phe Lys Gly Arg Val Thr Met Thr Arg Asp Thr Ser Thr Ser
                85                  90                  95

Thr Val Tyr Met Glu Leu Ser Ser Leu Arg Ser Glu Asp Thr Ala Val
            100                 105                 110

Tyr Tyr Cys Ala Gly Gly Asp Tyr Glu Asp Tyr Trp Gly Gln Gly Thr
        115                 120                 125

Thr Leu Thr Val Ser Ser Ala Ser Thr Lys Gly Pro Ser Val Phe Pro
130                 135                 140

Leu Ala Pro Cys Ser Arg Ser Thr Ser Glu Ser Thr Ala Ala Leu Gly
145                 150                 155                 160

Cys Leu Val Lys Asp Tyr Phe Pro Glu Pro Val Thr Val Ser Trp Asn
                165                 170                 175

Ser Gly Ala Leu Thr Ser Gly Val His Thr Phe Pro Ala Val Leu Gln
            180                 185                 190

Ser Ser Gly Leu Tyr Ser Leu Ser Ser Val Val Thr Val Pro Ser Ser
        195                 200                 205

Ser Leu Gly Thr Lys Thr Tyr Thr Cys Asn Val Asp His Lys Pro Ser
210                 215                 220

Asn Thr Lys Val Asp Lys Arg Val Glu Ser Lys Tyr Gly Pro Pro Cys
225                 230                 235                 240

Pro Pro Cys Pro Ala Pro Glu Phe Leu Gly Gly Pro Ser Val Phe Leu
                245                 250                 255

Phe Pro Pro Lys Pro Lys Asp Thr Leu Met Ile Ser Arg Thr Pro Glu
            260                 265                 270

Val Thr Cys Val Val Val Asp Val Ser Gln Glu Asp Pro Glu Val Gln
        275                 280                 285

Phe Asn Trp Tyr Val Asp Gly Val Glu Val His Asn Ala Lys Thr Lys
290                 295                 300

Pro Arg Glu Glu Gln Phe Asn Ser Thr Tyr Arg Val Val Ser Val Leu
305                 310                 315                 320

Thr Val Leu His Gln Asp Trp Leu Asn Gly Lys Glu Tyr Lys Cys Lys
                325                 330                 335

Val Ser Asn Lys Gly Leu Pro Ser Ser Ile Glu Lys Thr Ile Ser Lys
            340                 345                 350

Ala Lys Gly Gln Pro Arg Glu Pro Gln Val Tyr Thr Leu Pro Pro Ser
        355                 360                 365

Gln Glu Glu Met Thr Lys Asn Gln Val Ser Leu Thr Cys Leu Val Lys
370                 375                 380

Gly Phe Tyr Pro Ser Asp Ile Ala Val Glu Trp Glu Ser Asn Gly Gln
385                 390                 395                 400

Pro Glu Asn Asn Tyr Lys Thr Thr Pro Pro Val Leu Asp Ser Asp Gly
            405                 410                 415

Ser Phe Phe Leu Tyr Ser Arg Leu Thr Val Asp Lys Ser Arg Trp Gln
        420                 425                 430

Glu Gly Asn Val Phe Ser Cys Ser Val Met His Glu Ala Leu His Asn
    435                 440                 445

His Tyr Thr Gln Lys Ser Leu Ser Leu Ser Leu Gly Lys
450                 455                 460

<210> SEQ ID NO 40
<211> LENGTH: 233
<212> TYPE: PRT
<213> ORGANISM: Artificial Sequence
<220> FEATURE:
<223> OTHER INFORMATION: chimeric antibody molecules

<400> SEQUENCE: 40

Met Val Ser Ser Ala Gln Phe Leu Gly Leu Leu Leu Cys Phe Gln
1               5                   10                  15

Gly Thr Arg Cys Glu Asn Val Leu Thr Gln Ser Pro Ala Ile Met Ser
            20                  25                  30

Ala Ser Leu Gly Glu Lys Val Thr Met Ser Cys Arg Ala Ser Ser Ser
        35                  40                  45

Val Asn Tyr Met Tyr Trp Tyr Gln Gln Lys Ser Asp Ala Ser Pro Lys
    50                  55                  60

Leu Trp Ile Tyr Tyr Thr Ser Asn Leu Ala Pro Gly Val Pro Asp Arg
65                  70                  75                  80

Phe Ser Gly Ser Gly Ser Gly Asn Ser Tyr Ser Leu Thr Ile Ser Ser
                85                  90                  95

Met Glu Gly Glu Asp Ala Ala Thr Tyr Tyr Cys Gln Gln Phe Ser Ser
            100                 105                 110

Pro Pro Phe Thr Phe Gly Ser Gly Thr Lys Leu Glu Ile Lys Arg Thr
        115                 120                 125

Val Ala Ala Pro Ser Val Phe Ile Phe Pro Pro Ser Asp Glu Gln Leu
    130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
            180                 185                 190

Ser Leu Ser Ser Thr Leu Thr Leu Ser Lys Ala Asp Tyr Glu Lys His
        195                 200                 205

Lys Val Tyr Ala Cys Glu Val Thr His Gln Gly Leu Ser Ser Pro Val
    210                 215                 220

Thr Lys Ser Phe Asn Arg Gly Glu Cys
225                 230

<210> SEQ ID NO 41
<211> LENGTH: 233
<212> TYPE: PRT
<213> ORGANISM: Artificial Sequence
<220> FEATURE:
<223> OTHER INFORMATION: chimeric antibody molecules

<400> SEQUENCE: 41

Met Val Ser Ser Ala Gln Phe Leu Gly Leu Leu Leu Cys Phe Gln
1               5                   10                  15

Gly Thr Arg Cys Glu Ile Val Leu Thr Gln Ser Pro Ser Leu Ser
                20                  25                  30

Ala Ser Val Gly Asp Arg Val Thr Ile Thr Cys Arg Ala Ser Ser
            35                  40                  45

Val Asn Tyr Met Tyr Trp Tyr Gln Gln Lys Pro Gly Lys Ala Pro Lys
50                      55                  60

Leu Leu Ile Tyr Tyr Thr Ser Asn Leu Ala Pro Gly Val Pro Ser Arg
65                  70                  75                  80

Phe Ser Gly Ser Gly Ser Gly Thr Asp Phe Thr Leu Thr Ile Ser Ser
                85                  90                  95

Leu Gln Pro Glu Asp Phe Ala Thr Tyr Tyr Cys Gln Gln Phe Ser Ser
                100                 105                 110

Pro Pro Phe Thr Phe Gly Gln Gly Thr Lys Leu Glu Ile Lys Arg Thr
                115                 120                 125

Val Ala Ala Pro Ser Val Phe Ile Phe Pro Ser Asp Glu Gln Leu
130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
                180                 185                 190

Ser Leu Ser Ser Thr Leu Thr Leu Ser Lys Ala Asp Tyr Glu Lys His
                195                 200                 205

Lys Val Tyr Ala Cys Glu Val Thr His Gln Gly Leu Ser Ser Pro Val
                210                 215                 220

Thr Lys Ser Phe Asn Arg Gly Glu Cys
225                 230

<210> SEQ ID NO 42
<211> LENGTH: 233
<212> TYPE: PRT
<213> ORGANISM: Artificial Sequence
<220> FEATURE:
<223> OTHER INFORMATION: chimeric antibody molecules

<400> SEQUENCE: 42

Met Val Ser Ser Ala Gln Phe Leu Gly Leu Leu Leu Cys Phe Gln
1               5                   10                  15

Gly Thr Arg Cys Glu Ile Val Leu Thr Gln Ser Pro Ala Thr Leu Ser
                20                  25                  30

Leu Ser Pro Gly Glu Arg Ala Thr Leu Ser Cys Arg Ala Ser Ser
            35                  40                  45

Val Asn Tyr Met Tyr Trp Tyr Gln Gln Lys Pro Gly Gln Ala Pro Arg
50                      55                  60

Leu Leu Ile Tyr Tyr Thr Ser Asn Leu Ala Pro Gly Ile Pro Ala Arg
65                  70                  75                  80

Phe Ser Gly Ser Gly Ser Gly Thr Asp Phe Thr Leu Thr Ile Ser Ser
                85                  90                  95

Leu Glu Pro Glu Asp Phe Ala Val Tyr Tyr Cys Gln Gln Phe Ser Ser
                100                 105                 110

```
Pro Pro Phe Thr Phe Gly Pro Gly Thr Lys Val Asp Ile Lys Arg Thr
            115                 120                 125

Val Ala Ala Pro Ser Val Phe Ile Phe Pro Pro Ser Asp Glu Gln Leu
        130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
            180                 185                 190

Ser Leu Ser Ser Thr Leu Thr Leu Ser Lys Ala Asp Tyr Glu Lys His
        195                 200                 205

Lys Val Tyr Ala Cys Glu Val Thr His Gln Gly Leu Ser Ser Pro Val
            210                 215                 220

Thr Lys Ser Phe Asn Arg Gly Glu Cys
225                 230
```

<210> SEQ ID NO 43
<211> LENGTH: 233
<212> TYPE: PRT
<213> ORGANISM: Artificial Sequence
<220> FEATURE:
<223> OTHER INFORMATION: chimeric antibody molecules

<400> SEQUENCE: 43

```
Met Val Ser Ser Ala Gln Phe Leu Gly Leu Leu Leu Leu Cys Phe Gln
1               5                   10                  15

Gly Thr Arg Cys Asp Ile Val Leu Thr Gln Ser Pro Glu Ser Leu Ala
            20                  25                  30

Val Ser Leu Gly Glu Arg Ala Thr Ile Asn Cys Arg Ala Ser Ser Ser
        35                  40                  45

Val Asn Tyr Met Tyr Trp Tyr Gln Gln Lys Ser Gly Gln Pro Pro Lys
    50                  55                  60

Leu Leu Ile Tyr Tyr Thr Ser Asn Leu Ala Pro Gly Val Pro Glu Arg
65                  70                  75                  80

Phe Ser Gly Ser Gly Ser Gly Thr Asp Phe Thr Leu Thr Ile Ser Ser
                85                  90                  95

Leu Gln Ala Glu Asp Val Ala Val Tyr Tyr Cys Gln Gln Phe Ser Ser
            100                 105                 110

Pro Pro Phe Thr Phe Gly Gln Gly Thr Lys Leu Glu Ile Lys Arg Thr
            115                 120                 125

Val Ala Ala Pro Ser Val Phe Ile Phe Pro Pro Ser Asp Glu Gln Leu
        130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
            180                 185                 190

Ser Leu Ser Ser Thr Leu Thr Leu Ser Lys Ala Asp Tyr Glu Lys His
        195                 200                 205

Lys Val Tyr Ala Cys Glu Val Thr His Gln Gly Leu Ser Ser Pro Val
            210                 215                 220

Thr Lys Ser Phe Asn Arg Gly Glu Cys
225                 230
```

```
<210> SEQ ID NO 44
<211> LENGTH: 233
<212> TYPE: PRT
<213> ORGANISM: Artificial Sequence
<220> FEATURE:
<223> OTHER INFORMATION: chimeric antibody molecules

<400> SEQUENCE: 44

Met Val Ser Ser Ala Gln Phe Leu Gly Leu Leu Leu Leu Cys Phe Gln
1               5                   10                  15

Gly Thr Arg Cys Glu Leu Val Leu Thr Gln Ser Pro Gly Thr Leu Ser
                20                  25                  30

Leu Ser Pro Gly Glu Arg Ala Thr Leu Ser Cys Arg Ala Ser Ser Ser
            35                  40                  45

Val Asn Tyr Met Tyr Trp Tyr Gln Gln Lys Pro Gly Gln Ala Pro Arg
    50                  55                  60

Leu Leu Ile Tyr Tyr Thr Ser Asn Leu Ala Pro Gly Ile Pro Asp Arg
65                  70                  75                  80

Phe Ser Gly Ser Gly Ser Gly Thr Asp Phe Thr Leu Thr Ile Ser Ser
                85                  90                  95

Leu Gln Pro Glu Asp Ala Ala Thr Tyr Tyr Cys Gln Gln Phe Ser Ser
            100                 105                 110

Pro Pro Phe Thr Phe Gly Gln Gly Thr Lys Leu Glu Ile Lys Arg Thr
        115                 120                 125

Val Ala Ala Pro Ser Val Phe Ile Phe Pro Pro Ser Asp Glu Gln Leu
    130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
            180                 185                 190

Ser Leu Ser Ser Thr Leu Thr Leu Ser Lys Ala Asp Tyr Glu Lys His
        195                 200                 205

Lys Val Tyr Ala Cys Glu Val Thr His Gln Gly Leu Ser Ser Pro Val
    210                 215                 220

Thr Lys Ser Phe Asn Arg Gly Glu Cys
225                 230

<210> SEQ ID NO 45
<211> LENGTH: 233
<212> TYPE: PRT
<213> ORGANISM: Artificial Sequence
<220> FEATURE:
<223> OTHER INFORMATION: chimeric antibody molecules

<400> SEQUENCE: 45

Met Val Ser Ser Ala Gln Phe Leu Gly Leu Leu Leu Leu Cys Phe Gln
1               5                   10                  15

Gly Thr Arg Cys Glu Ile Val Leu Thr Gln Ser Pro Ala Thr Leu Ser
                20                  25                  30

Leu Ser Pro Gly Glu Arg Ala Thr Leu Ser Cys Arg Ala Ser Ser Ser
            35                  40                  45

Val Asn Tyr Met Tyr Trp Tyr Gln Gln Lys Pro Gly Gln Ala Pro Arg
    50                  55                  60
```

```
Leu Leu Ile Tyr Tyr Thr Ser Asn Leu Ala Pro Gly Ile Pro Ala Arg
 65                  70                  75                  80

Phe Ser Gly Ser Gly Ser Gly Thr Asp Phe Thr Leu Thr Ile Ser Ser
                 85                  90                  95

Leu Glu Pro Glu Asp Phe Ala Val Tyr Tyr Cys Gln Gln Phe Ser Ser
            100                 105                 110

Pro Pro Phe Thr Phe Gly Ser Gly Thr Lys Leu Glu Ile Lys Arg Thr
        115                 120                 125

Val Ala Ala Pro Ser Val Phe Ile Phe Pro Pro Ser Asp Glu Gln Leu
130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
            180                 185                 190

Ser Leu Ser Ser Thr Leu Thr Leu Ser Lys Ala Asp Tyr Glu Lys His
        195                 200                 205

Lys Val Tyr Ala Cys Glu Val Thr His Gln Gly Leu Ser Ser Pro Val
210                 215                 220

Thr Lys Ser Phe Asn Arg Gly Glu Cys
225                 230

<210> SEQ ID NO 46
<211> LENGTH: 469
<212> TYPE: PRT
<213> ORGANISM: Artificial Sequence
<220> FEATURE:
<223> OTHER INFORMATION: chimeric antibody molecules

<400> SEQUENCE: 46

Met Gly Trp Thr Leu Val Phe Leu Phe Leu Leu Ser Val Thr Ala Gly
 1               5                  10                  15

Val His Ser Glu Val Lys Leu Val Glu Ser Gly Gly Gly Leu Val Asn
                20                  25                  30

Pro Gly Gly Ser Leu Lys Leu Ser Cys Ala Ala Ser Ala Phe Thr Phe
            35                  40                  45

Ser Thr Tyr Ala Met Ser Trp Val Arg Gln Thr Pro Glu Lys Arg Leu
        50                  55                  60

Glu Trp Val Thr Ser Ile Ser Ser Gly Gly Arg Thr Tyr Tyr Pro Asp
 65                  70                  75                  80

Ser Val Lys Gly Arg Phe Asn Ile Ser Arg Asp Asn Ala Arg Asn Ile
                 85                  90                  95

Leu Tyr Leu Gln Met Ser Thr Leu Arg Ser Glu Asp Thr Ala Met Tyr
            100                 105                 110

Tyr Cys Ala Arg Ser Tyr Gly Asn Tyr Val Gly Tyr Val Met Asp Tyr
        115                 120                 125

Trp Gly Gln Gly Thr Ser Val Thr Val Ser Ser Ala Ser Thr Lys Gly
130                 135                 140

Pro Ser Val Phe Pro Leu Ala Pro Ser Ser Lys Ser Thr Ser Gly Gly
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190
```

```
Pro Ala Val Leu Gln Ser Ser Gly Leu Tyr Ser Leu Ser Val Val
        195                 200                 205

Thr Val Pro Ser Ser Ser Leu Gly Thr Gln Thr Tyr Ile Cys Asn Val
    210                 215                 220

Asn His Lys Pro Ser Asn Thr Lys Val Asp Lys Lys Val Glu Pro Lys
225                 230                 235                 240

Ser Cys Asp Lys Thr His Thr Cys Pro Pro Cys Pro Ala Pro Glu Leu
            245                 250                 255

Leu Gly Gly Pro Ser Val Phe Leu Phe Pro Pro Lys Pro Lys Asp Thr
        260                 265                 270

Leu Met Ile Ser Arg Thr Pro Glu Val Thr Cys Val Val Val Asp Val
    275                 280                 285

Ser His Glu Asp Pro Glu Val Lys Phe Asn Trp Tyr Val Asp Gly Val
290                 295                 300

Glu Val His Asn Ala Lys Thr Lys Pro Arg Glu Glu Gln Tyr Asn Ser
305                 310                 315                 320

Thr Tyr Arg Val Val Ser Val Leu Thr Val Leu His Gln Asp Trp Leu
            325                 330                 335

Asn Gly Lys Glu Tyr Lys Cys Lys Val Ser Asn Lys Ala Leu Pro Ala
        340                 345                 350

Pro Ile Glu Lys Thr Ile Ser Lys Ala Lys Gly Gln Pro Arg Glu Pro
    355                 360                 365

Gln Val Tyr Thr Leu Pro Pro Ser Arg Asp Glu Leu Thr Lys Asn Gln
370                 375                 380

Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
            405                 410                 415

Pro Pro Val Leu Asp Ser Asp Gly Ser Phe Phe Leu Tyr Ser Lys Leu
        420                 425                 430

Thr Val Asp Lys Ser Arg Trp Gln Gln Gly Asn Val Phe Ser Cys Ser
    435                 440                 445

Val Met His Glu Ala Leu His Asn His Tyr Thr Gln Lys Ser Leu Ser
450                 455                 460

Leu Ser Pro Gly Lys
465

<210> SEQ ID NO 47
<211> LENGTH: 469
<212> TYPE: PRT
<213> ORGANISM: Artificial Sequence
<220> FEATURE:
<223> OTHER INFORMATION: chimeric antibody molecules

<400> SEQUENCE: 47

Met Gly Trp Thr Leu Val Phe Leu Phe Leu Leu Ser Val Thr Ala Gly
1               5                   10                  15

Val His Ser Glu Val Gln Leu Val Glu Ser Gly Gly Gly Leu Val Gln
            20                  25                  30

Pro Gly Gly Ser Leu Arg Leu Ser Cys Ala Ala Ser Ala Phe Thr Phe
        35                  40                  45

Ser Thr Tyr Ala Met Ser Trp Val Arg Gln Ala Pro Gly Lys Gly Leu
    50                  55                  60

Glu Trp Val Ser Ser Ile Ser Ser Gly Gly Arg Thr Tyr Tyr Pro Asp
65                  70                  75                  80
```

Ser Val Lys Gly Arg Phe Thr Ile Ser Arg Asp Asn Ser Lys Asn Thr
            85                  90                  95

Leu Tyr Leu Gln Met Asn Ser Leu Arg Ala Glu Asp Thr Ala Val Tyr
            100                 105                 110

Tyr Cys Ala Arg Ser Tyr Gly Asn Tyr Val Gly Tyr Val Met Asp Tyr
            115                 120                 125

Trp Gly Gln Gly Thr Leu Val Thr Val Ser Ser Ala Ser Thr Lys Gly
130                 135                 140

Pro Ser Val Phe Pro Leu Ala Pro Ser Ser Lys Ser Thr Ser Gly Gly
145                 150                 155                 160

Thr Ala Ala Leu Gly Cys Leu Val Lys Asp Tyr Phe Pro Glu Pro Val
            165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
            195                 200                 205

Thr Val Pro Ser Ser Ser Leu Gly Thr Gln Thr Tyr Ile Cys Asn Val
            210                 215                 220

Asn His Lys Pro Ser Asn Thr Lys Val Asp Lys Lys Val Glu Pro Lys
225                 230                 235                 240

Ser Cys Asp Lys Thr His Thr Cys Pro Pro Cys Pro Ala Pro Glu Leu
            245                 250                 255

Leu Gly Gly Pro Ser Val Phe Leu Phe Pro Pro Lys Pro Lys Asp Thr
            260                 265                 270

Leu Met Ile Ser Arg Thr Pro Glu Val Thr Cys Val Val Val Asp Val
            275                 280                 285

Ser His Glu Asp Pro Glu Val Lys Phe Asn Trp Tyr Val Asp Gly Val
            290                 295                 300

Glu Val His Asn Ala Lys Thr Lys Pro Arg Glu Glu Gln Tyr Asn Ser
305                 310                 315                 320

Thr Tyr Arg Val Val Ser Val Leu Thr Val Leu His Gln Asp Trp Leu
            325                 330                 335

Asn Gly Lys Glu Tyr Lys Cys Lys Val Ser Asn Lys Ala Leu Pro Ala
            340                 345                 350

Pro Ile Glu Lys Thr Ile Ser Lys Ala Lys Gly Gln Pro Arg Glu Pro
            355                 360                 365

Gln Val Tyr Thr Leu Pro Pro Ser Arg Asp Glu Leu Thr Lys Asn Gln
            370                 375                 380

Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
            405                 410                 415

Pro Pro Val Leu Asp Ser Asp Gly Ser Phe Phe Leu Tyr Ser Lys Leu
            420                 425                 430

Thr Val Asp Lys Ser Arg Trp Gln Gln Gly Asn Val Phe Ser Cys Ser
            435                 440                 445

Val Met His Glu Ala Leu His Asn His Tyr Thr Gln Lys Ser Leu Ser
450                 455                 460

Leu Ser Pro Gly Lys
465

<210> SEQ ID NO 48
<211> LENGTH: 469

-continued

```
<212> TYPE: PRT
<213> ORGANISM: Artificial Sequence
<220> FEATURE:
<223> OTHER INFORMATION: chimeric antibody molecules

<400> SEQUENCE: 48

Met Gly Trp Thr Leu Val Phe Leu Phe Leu Ser Val Thr Ala Gly
1               5                   10                  15

Val His Ser Gln Val Lys Leu Leu Glu Ser Gly Gly Gly Leu Val Gln
            20                  25                  30

Pro Gly Gly Ser Leu Arg Leu Ser Cys Ser Ala Ser Ala Phe Thr Phe
            35                  40                  45

Ser Thr Tyr Ala Met Ser Trp Val Arg Gln Ala Pro Gly Lys Gly Leu
        50                  55                  60

Glu Tyr Val Ser Ser Ile Ser Ser Gly Gly Arg Thr Tyr Tyr Pro Asp
65                  70                  75                  80

Ser Val Lys Gly Arg Phe Thr Ile Ser Arg Asp Asn Ser Lys Asn Thr
                85                  90                  95

Val Tyr Leu Gln Met Ser Ser Leu Arg Ala Glu Asp Thr Ala Val Tyr
            100                 105                 110

Tyr Cys Ala Arg Ser Tyr Gly Asn Tyr Val Gly Tyr Val Met Asp Tyr
            115                 120                 125

Trp Gly Gln Gly Thr Leu Val Thr Val Ser Ser Ala Ser Thr Lys Gly
130                 135                 140

Pro Ser Val Phe Pro Leu Ala Pro Ser Ser Lys Ser Thr Ser Gly Gly
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
            195                 200                 205

Thr Val Pro Ser Ser Ser Leu Gly Thr Gln Thr Tyr Ile Cys Asn Val
210                 215                 220

Asn His Lys Pro Ser Asn Thr Lys Val Asp Lys Lys Val Glu Pro Lys
225                 230                 235                 240

Ser Cys Asp Lys Thr His Thr Cys Pro Pro Cys Pro Ala Pro Glu Leu
                245                 250                 255

Leu Gly Gly Pro Ser Val Phe Leu Phe Pro Pro Lys Pro Lys Asp Thr
            260                 265                 270

Leu Met Ile Ser Arg Thr Pro Glu Val Thr Cys Val Val Val Asp Val
        275                 280                 285

Ser His Glu Asp Pro Glu Val Lys Phe Asn Trp Tyr Val Asp Gly Val
290                 295                 300

Glu Val His Asn Ala Lys Thr Lys Pro Arg Glu Glu Gln Tyr Asn Ser
305                 310                 315                 320

Thr Tyr Arg Val Val Ser Val Leu Thr Val Leu His Gln Asp Trp Leu
                325                 330                 335

Asn Gly Lys Glu Tyr Lys Cys Lys Val Ser Asn Lys Ala Leu Pro Ala
            340                 345                 350

Pro Ile Glu Lys Thr Ile Ser Lys Ala Lys Gly Gln Pro Arg Glu Pro
        355                 360                 365

Gln Val Tyr Thr Leu Pro Pro Ser Arg Asp Glu Leu Thr Lys Asn Gln
370                 375                 380
```

```
Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
            405                 410                 415

Pro Pro Val Leu Asp Ser Asp Gly Ser Phe Phe Leu Tyr Ser Lys Leu
            420                 425                 430

Thr Val Asp Lys Ser Arg Trp Gln Gln Gly Asn Val Phe Ser Cys Ser
            435                 440                 445

Val Met His Glu Ala Leu His Asn His Tyr Thr Gln Lys Ser Leu Ser
450                 455                 460

Leu Ser Pro Gly Lys
465
```

<210> SEQ ID NO 49
<211> LENGTH: 468
<212> TYPE: PRT
<213> ORGANISM: Artificial Sequence
<220> FEATURE:
<223> OTHER INFORMATION: chimeric antibody molecules

<400> SEQUENCE: 49

```
Met Gly Trp Thr Leu Val Phe Leu Phe Leu Leu Ser Val Thr Ala Gly
1               5                   10                  15

Val His Ser Val Gln Leu Val Glu Ser Gly Gly Gly Leu Val Gln Pro
            20                  25                  30

Gly Gly Ser Leu Arg Leu Ser Cys Ala Ala Ser Ala Phe Thr Phe Ser
        35                  40                  45

Thr Tyr Ala Met Ser Trp Val Arg Gln Ala Pro Glu Lys Gly Leu Glu
    50                  55                  60

Trp Val Ser Ser Ile Ser Ser Gly Gly Arg Thr Tyr Tyr Pro Asp Ser
65                  70                  75                  80

Val Lys Gly Arg Phe Thr Ile Ser Arg Asp Asn Ser Lys Asn Thr Leu
                85                  90                  95

Tyr Leu Gln Met Asn Ser Leu Arg Ala Glu Asp Thr Ala Arg Tyr Tyr
            100                 105                 110

Cys Ala Arg Ser Tyr Gly Asn Tyr Val Gly Tyr Val Met Asp Tyr Trp
        115                 120                 125

Gly Gln Gly Thr Leu Val Thr Val Ser Ser Ala Ser Thr Lys Gly Pro
130                 135                 140

Ser Val Phe Pro Leu Ala Pro Ser Ser Lys Ser Thr Ser Gly Gly Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
            180                 185                 190

Ala Val Leu Gln Ser Ser Gly Leu Tyr Ser Leu Ser Ser Val Val Thr
        195                 200                 205

Val Pro Ser Ser Ser Leu Gly Thr Gln Thr Tyr Ile Cys Asn Val Asn
    210                 215                 220

His Lys Pro Ser Asn Thr Lys Val Asp Lys Lys Val Glu Pro Lys Ser
225                 230                 235                 240

Cys Asp Lys Thr His Thr Cys Pro Pro Cys Pro Ala Pro Glu Leu Leu
                245                 250                 255

Gly Gly Pro Ser Val Phe Leu Phe Pro Pro Lys Pro Lys Asp Thr Leu
            260                 265                 270
```

```
Met Ile Ser Arg Thr Pro Glu Val Thr Cys Val Val Val Asp Val Ser
            275                 280                 285

His Glu Asp Pro Glu Val Lys Phe Asn Trp Tyr Val Asp Gly Val Glu
    290                 295                 300

Val His Asn Ala Lys Thr Lys Pro Arg Glu Glu Gln Tyr Asn Ser Thr
305                 310                 315                 320

Tyr Arg Val Val Ser Val Leu Thr Val Leu His Gln Asp Trp Leu Asn
                325                 330                 335

Gly Lys Glu Tyr Lys Cys Lys Val Ser Asn Lys Ala Leu Pro Ala Pro
            340                 345                 350

Ile Glu Lys Thr Ile Ser Lys Ala Lys Gly Gln Pro Arg Glu Pro Gln
            355                 360                 365

Val Tyr Thr Leu Pro Pro Ser Arg Asp Glu Leu Thr Lys Asn Gln Val
    370                 375                 380

Ser Leu Thr Cys Leu Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
                405                 410                 415

Pro Val Leu Asp Ser Asp Gly Ser Phe Phe Leu Tyr Ser Lys Leu Thr
            420                 425                 430

Val Asp Lys Ser Arg Trp Gln Gln Gly Asn Val Phe Ser Cys Ser Val
            435                 440                 445

Met His Glu Ala Leu His Asn His Tyr Thr Gln Lys Ser Leu Ser Leu
            450                 455                 460

Ser Pro Gly Lys
465

<210> SEQ ID NO 50
<211> LENGTH: 469
<212> TYPE: PRT
<213> ORGANISM: Artificial Sequence
<220> FEATURE:
<223> OTHER INFORMATION: chimeric antibody molecules

<400> SEQUENCE: 50

Met Gly Trp Thr Leu Val Phe Leu Phe Leu Leu Ser Val Thr Ala Gly
1               5                   10                  15

Val His Ser Glu Val Gln Leu Val Glu Ser Gly Gly Gly Leu Val Gln
            20                  25                  30

Pro Gly Gly Ser Leu Arg Leu Ser Cys Ala Ala Ser Ala Phe Thr Phe
        35                  40                  45

Ser Thr Tyr Ala Met Ser Trp Val Arg Gln Ala Pro Gly Lys Gly Leu
    50                  55                  60

Glu Trp Val Ser Ser Ile Ser Ser Gly Gly Arg Thr Tyr Tyr Pro Asp
65                  70                  75                  80

Ser Val Lys Gly Arg Phe Thr Ile Ser Arg Asp Asn Ser Lys Asn Thr
                85                  90                  95

Leu Phe Leu Arg Met Asn Ser Leu Arg Val Glu Asp Thr Ala Val Tyr
            100                 105                 110

Phe Cys Ala Arg Ser Tyr Gly Asn Tyr Val Gly Tyr Val Met Asp Tyr
        115                 120                 125

Trp Gly Gln Gly Thr Leu Val Thr Val Ser Ser Ala Ser Thr Lys Gly
    130                 135                 140

Pro Ser Val Phe Pro Leu Ala Pro Ser Ser Lys Ser Thr Ser Gly Gly
145                 150                 155                 160
```

-continued

```
Thr Ala Ala Leu Gly Cys Leu Val Lys Asp Tyr Phe Pro Glu Pro Val
            165                 170                 175

Thr Val Ser Trp Asn Ser Gly Ala Leu Thr Ser Gly Val His Thr Phe
        180                 185                 190

Pro Ala Val Leu Gln Ser Ser Gly Leu Tyr Ser Leu Ser Ser Val Val
        195                 200                 205

Thr Val Pro Ser Ser Ser Leu Gly Thr Gln Thr Tyr Ile Cys Asn Val
        210                 215                 220

Asn His Lys Pro Ser Asn Thr Lys Val Asp Lys Val Glu Pro Lys
225                 230                 235                 240

Ser Cys Asp Lys Thr His Thr Cys Pro Pro Cys Pro Ala Pro Glu Leu
                245                 250                 255

Leu Gly Gly Pro Ser Val Phe Leu Phe Pro Pro Lys Pro Lys Asp Thr
            260                 265                 270

Leu Met Ile Ser Arg Thr Pro Glu Val Thr Cys Val Val Val Asp Val
        275                 280                 285

Ser His Glu Asp Pro Glu Val Lys Phe Asn Trp Tyr Val Asp Gly Val
        290                 295                 300

Glu Val His Asn Ala Lys Thr Lys Pro Arg Glu Glu Gln Tyr Asn Ser
305                 310                 315                 320

Thr Tyr Arg Val Val Ser Val Leu Thr Val Leu His Gln Asp Trp Leu
                325                 330                 335

Asn Gly Lys Glu Tyr Lys Cys Lys Val Ser Asn Lys Ala Leu Pro Ala
            340                 345                 350

Pro Ile Glu Lys Thr Ile Ser Lys Ala Lys Gly Gln Pro Arg Glu Pro
        355                 360                 365

Gln Val Tyr Thr Leu Pro Pro Ser Arg Asp Glu Leu Thr Lys Asn Gln
        370                 375                 380

Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
                405                 410                 415

Pro Pro Val Leu Asp Ser Asp Gly Ser Phe Phe Leu Tyr Ser Lys Leu
            420                 425                 430

Thr Val Asp Lys Ser Arg Trp Gln Gln Gly Asn Val Phe Ser Cys Ser
        435                 440                 445

Val Met His Glu Ala Leu His Asn His Tyr Thr Gln Lys Ser Leu Ser
        450                 455                 460

Leu Ser Pro Gly Lys
465

<210> SEQ ID NO 51
<211> LENGTH: 469
<212> TYPE: PRT
<213> ORGANISM: Artificial Sequence
<220> FEATURE:
<223> OTHER INFORMATION: chimeric antibody molecules

<400> SEQUENCE: 51

Met Gly Trp Thr Leu Val Phe Leu Phe Leu Leu Ser Val Thr Ala Gly
1               5                   10                  15

Val His Ser Glu Val Gln Leu Leu Glu Ser Gly Gly Gly Leu Val Gln
            20                  25                  30

Pro Gly Gly Ser Leu Arg Leu Ser Cys Ala Ala Ser Ala Phe Thr Phe
        35                  40                  45
```

```
Ser Thr Tyr Ala Met Ser Trp Val Arg Gln Ala Pro Gly Lys Gly Leu
     50                  55                  60

Glu Trp Val Ser Ser Ile Ser Ser Gly Gly Arg Thr Tyr Tyr Pro Asp
 65                  70                  75                  80

Ser Val Lys Gly Arg Phe Thr Ile Ser Arg Asp Asn Ser Lys Asn Thr
                 85                  90                  95

Leu Tyr Leu Gln Met Asn Ser Leu Arg Ala Glu Asp Thr Ala Val Tyr
            100                 105                 110

Tyr Cys Ala Arg Ser Tyr Gly Asn Tyr Val Gly Tyr Val Met Asp Tyr
            115                 120                 125

Trp Gly Gln Gly Thr Ser Val Thr Val Ser Ser Ala Ser Thr Lys Gly
    130                 135                 140

Pro Ser Val Phe Pro Leu Ala Pro Ser Ser Lys Ser Thr Ser Gly Gly
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
            195                 200                 205

Thr Val Pro Ser Ser Ser Leu Gly Thr Gln Thr Tyr Ile Cys Asn Val
    210                 215                 220

Asn His Lys Pro Ser Asn Thr Lys Val Asp Lys Lys Val Glu Pro Lys
225                 230                 235                 240

Ser Cys Asp Lys Thr His Thr Cys Pro Pro Cys Pro Ala Pro Glu Leu
                245                 250                 255

Leu Gly Gly Pro Ser Val Phe Leu Phe Pro Pro Lys Pro Lys Asp Thr
            260                 265                 270

Leu Met Ile Ser Arg Thr Pro Glu Val Thr Cys Val Val Val Asp Val
            275                 280                 285

Ser His Glu Asp Pro Glu Val Lys Phe Asn Trp Tyr Val Asp Gly Val
    290                 295                 300

Glu Val His Asn Ala Lys Thr Lys Pro Arg Glu Glu Gln Tyr Asn Ser
305                 310                 315                 320

Thr Tyr Arg Val Val Ser Val Leu Thr Val Leu His Gln Asp Trp Leu
                325                 330                 335

Asn Gly Lys Glu Tyr Lys Cys Lys Val Ser Asn Lys Ala Leu Pro Ala
            340                 345                 350

Pro Ile Glu Lys Thr Ile Ser Lys Ala Lys Gly Gln Pro Arg Glu Pro
            355                 360                 365

Gln Val Tyr Thr Leu Pro Pro Ser Arg Asp Glu Leu Thr Lys Asn Gln
    370                 375                 380

Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
                405                 410                 415

Pro Pro Val Leu Asp Ser Asp Gly Ser Phe Phe Leu Tyr Ser Lys Leu
            420                 425                 430

Thr Val Asp Lys Ser Arg Trp Gln Gln Gly Asn Val Phe Ser Cys Ser
            435                 440                 445

Val Met His Glu Ala Leu His Asn His Tyr Thr Gln Lys Ser Leu Ser
    450                 455                 460
```

Leu Ser Pro Gly Lys
465

<210> SEQ ID NO 52
<211> LENGTH: 234
<212> TYPE: PRT
<213> ORGANISM: Artificial Sequence
<220> FEATURE:
<223> OTHER INFORMATION: chimeric antibody molecules

<400> SEQUENCE: 52

Met Val Ser Ser Ala Gln Phe Leu Gly Leu Leu Leu Cys Phe Gln
1               5                   10                  15

Gly Thr Arg Cys Asp Ile Gln Met Thr Gln Ser Pro Ala Ser Leu Ser
            20                  25                  30

Ala Ser Val Gly Glu Thr Val Thr Ile Thr Cys Arg Ala Ser Asp Asn
        35                  40                  45

Ile Tyr Ser Tyr Phe Ala Trp Tyr Arg Gln Lys Gln Gly Asn Ser Pro
    50                  55                  60

Gln Leu Leu Val Tyr Asn Ala Lys Thr Leu Ala Glu Gly Val Pro Ser
65                  70                  75                  80

Arg Phe Ser Gly Ser Gly Ser Gly Thr His Phe Ser Leu Lys Ile Asn
                85                  90                  95

Asn Leu Gln Pro Glu Asp Phe Gly Thr Tyr Tyr Cys Gln His His Tyr
            100                 105                 110

Gly Pro Pro Trp Thr Phe Gly Gly Gly Thr Lys Leu Glu Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230

<210> SEQ ID NO 53
<211> LENGTH: 234
<212> TYPE: PRT
<213> ORGANISM: Artificial Sequence
<220> FEATURE:
<223> OTHER INFORMATION: chimeric antibody molecules

<400> SEQUENCE: 53

Met Val Ser Ser Ala Gln Phe Leu Gly Leu Leu Leu Cys Phe Gln
1               5                   10                  15

Gly Thr Arg Cys Asp Ile Val Met Thr Gln Ser Pro Ser Thr Leu Ser
            20                  25                  30

Ala Ser Val Gly Asp Arg Val Thr Val Thr Cys Arg Ala Ser Asp Asn
        35                  40                  45

Ile Tyr Ser Tyr Phe Ala Trp Tyr Gln Gln Lys Pro Gly Lys Ala Pro
 50                  55                  60

Asn Leu Leu Ile Tyr Asn Ala Lys Thr Leu Ala Glu Gly Val Pro Ser
65                  70                  75                  80

Arg Phe Ser Gly Ser Gly Ser Gly Thr Glu Phe Thr Leu Thr Ile Asn
                85                  90                  95

Ser Leu Gln Pro Asp Asp Phe Gly Thr Tyr Tyr Cys Gln His His Tyr
            100                 105                 110

Gly Pro Pro Trp Thr Phe Gly Gly Gly Thr Lys Val Asp Ile Lys Arg
                115                 120                 125

Thr Val Ala Ala Pro Ser Val Phe Ile Phe Pro Pro Ser Asp Glu Gln
            130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
                195                 200                 205

His Lys Val Tyr Ala Cys Glu Val Thr His Gln Gly Leu Ser Ser Pro
            210                 215                 220

Val Thr Lys Ser Phe Asn Arg Gly Glu Cys
225                 230

<210> SEQ ID NO 54
<211> LENGTH: 234
<212> TYPE: PRT
<213> ORGANISM: Artificial Sequence
<220> FEATURE:
<223> OTHER INFORMATION: chimeric antibody molecules

<400> SEQUENCE: 54

Met Val Ser Ser Ala Gln Phe Leu Gly Leu Leu Leu Cys Phe Gln
1               5                   10                  15

Gly Thr Arg Cys Asp Ile Gln Met Thr Gln Ser Pro Ser Ser Leu Ser
                20                  25                  30

Ala Ser Val Gly Asp Arg Val Thr Val Thr Cys Arg Ala Ser Asp Asn
            35                  40                  45

Ile Tyr Ser Tyr Phe Ala Trp Tyr Gln His Lys Pro Gly Asn Ala Pro
 50                  55                  60

Lys Leu Leu Ile Tyr Asn Ala Lys Thr Leu Ala Glu Gly Val Pro Ser
65                  70                  75                  80

Arg Phe Ser Gly Ser Gly Ser Gly Thr Asp Phe Thr Leu Thr Ile Ser
                85                  90                  95

Ser Leu Gln Pro Glu Asp Phe Ala Thr Tyr Tyr Cys Gln His His Tyr
            100                 105                 110

Gly Pro Pro Trp Thr Phe Gly Gln Gly Thr Lys Val Glu Ile Lys Arg
                115                 120                 125

Thr Val Ala Ala Pro Ser Val Phe Ile Phe Pro Pro Ser Asp Glu Gln
            130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230

<210> SEQ ID NO 55
<211> LENGTH: 234
<212> TYPE: PRT
<213> ORGANISM: Artificial Sequence
<220> FEATURE:
<223> OTHER INFORMATION: chimeric antibody molecules

<400> SEQUENCE: 55

Met Val Ser Ser Ala Gln Phe Leu Gly Leu Leu Leu Leu Cys Phe Gln
1               5                   10                  15

Gly Thr Arg Cys Asp Ile Val Met Thr Gln Ser Pro Phe Ser Leu Ser
            20                  25                  30

Ala Ser Val Gly Asp Arg Val Thr Ile Thr Cys Arg Ala Ser Asp Asn
        35                  40                  45

Ile Tyr Ser Tyr Phe Ala Trp Tyr Gln Gln Lys Pro Gly Thr Ala Pro
    50                  55                  60

Lys Leu Leu Ile Tyr Asn Ala Lys Thr Leu Ala Glu Gly Val Pro Ser
65                  70                  75                  80

Arg Phe Ser Gly Ser Gly Ser Gly Thr Asp Phe Thr Leu Thr Ile Ser
                85                  90                  95

Thr Leu Gln Pro Glu Asp Phe Ala Thr Tyr Tyr Cys Gln His His Tyr
            100                 105                 110

Gly Pro Pro Trp Thr Phe Gly Gln Gly Thr Lys Leu Glu Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230

<210> SEQ ID NO 56
<211> LENGTH: 234
<212> TYPE: PRT
<213> ORGANISM: Artificial Sequence
<220> FEATURE:
<223> OTHER INFORMATION: chimeric antibody molecules

<400> SEQUENCE: 56

```
Met Val Ser Ser Ala Gln Phe Leu Gly Leu Leu Leu Cys Phe Gln
1               5                   10                  15

Gly Thr Arg Cys Asp Ile Gln Met Thr Gln Ser Pro Ser Ser Leu Ser
            20                  25                  30

Ala Ser Val Gly Asp Arg Val Thr Ile Thr Cys Arg Ala Ser Asp Asn
            35                  40                  45

Ile Tyr Ser Tyr Phe Ala Trp Tyr Arg Gln Lys Pro Gly Lys Ala Pro
50                  55                  60

Lys Leu Leu Ile Tyr Asn Ala Lys Thr Leu Ala Glu Gly Val Pro Ser
65                  70                  75                  80

Arg Phe Ser Gly Ser Gly Ser Gly Thr Asp Phe Thr Leu Thr Ile Ser
                85                  90                  95

Ser Leu Gln Pro Glu Asp Phe Ala Thr Tyr Tyr Cys Gln His His Tyr
            100                 105                 110

Gly Pro Pro Trp Thr Phe Gly Gln Gly Thr Lys Leu Glu Ile Lys Arg
            115                 120                 125

Thr Val Ala Ala Pro Ser Val Phe Ile Phe Pro Pro Ser Asp Glu Gln
130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
            195                 200                 205

His Lys Val Tyr Ala Cys Glu Val Thr His Gln Gly Leu Ser Ser Pro
210                 215                 220

Val Thr Lys Ser Phe Asn Arg Gly Glu Cys
225                 230
```

<210> SEQ ID NO 57
<211> LENGTH: 234
<212> TYPE: PRT
<213> ORGANISM: Artificial Sequence
<220> FEATURE:
<223> OTHER INFORMATION: chimeric antibody molecules

<400> SEQUENCE: 57

```
Met Val Ser Ser Ala Gln Phe Leu Gly Leu Leu Leu Cys Phe Gln
1               5                   10                  15

Gly Thr Arg Cys Asp Ile Gln Met Thr Gln Ser Pro Ser Ser Leu Ser
            20                  25                  30

Ala Ser Val Gly Asp Arg Val Thr Ile Thr Cys Arg Ala Ser Asp Asn
            35                  40                  45

Ile Tyr Ser Tyr Phe Ala Trp Tyr Gln Gln Lys Pro Gly Lys Ala Pro
50                  55                  60

Lys Leu Leu Ile Tyr Asn Ala Lys Thr Leu Ala Glu Gly Val Pro Ser
65                  70                  75                  80

Arg Phe Ser Gly Ser Gly Ser Gly Thr Asp Phe Thr Leu Thr Ile Ser
                85                  90                  95

Ser Leu Gln Pro Glu Asp Phe Ala Thr Tyr Tyr Cys Gln His His Tyr
            100                 105                 110
```

-continued

```
Gly Pro Pro Trp Thr Phe Gly Gly Thr Lys Leu Glu Ile Lys Arg
        115                 120             125

Thr Val Ala Ala Pro Ser Val Phe Ile Phe Pro Pro Ser Asp Glu Gln
    130                 135             140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165             170                 175

Gly Asn Ser Gln Glu Ser Val Thr Glu Gln Asp Ser Lys Asp Ser Thr
            180             185                 190

Tyr Ser Leu Ser Ser Thr Leu Thr Leu Ser Lys Ala Asp Tyr Glu Lys
        195             200                 205

His Lys Val Tyr Ala Cys Glu Val Thr His Gln Gly Leu Ser Ser Pro
    210                 215             220

Val Thr Lys Ser Phe Asn Arg Gly Glu Cys
225                 230
```